(12) United States Patent
Lind et al.

(10) Patent No.: US 6,666,644 B1
(45) Date of Patent: Dec. 23, 2003

(54) DISPENSING DEVICE FOR DISPENSING UNITS OF PLATFORM-LOADED GOODS

(75) Inventors: Peter Michael Lind, Yountville, CA (US); Sean Rutledge, San Francisco, CA (US); Joshua Hanney, Antioch, CA (US); Nora McCallie, Greenbrae, CA (US); James Happ, Glen Ellen, CA (US)

(73) Assignee: Labcon, North America, San Rafael, CA (US)

( * ) Notice: Subject to any disclaimer, the term of this patent is extended or adjusted under 35 U.S.C. 154(b) by 0 days.

(21) Appl. No.: 09/483,384

(22) Filed: Jan. 13, 2000

(51) Int. Cl.[7] .............................................. B65G 59/06
(52) U.S. Cl. ..................................... 414/798; 414/798.1
(58) Field of Search .............................. 414/798, 798.1, 414/795.6, 797.4

(56) References Cited

U.S. PATENT DOCUMENTS

| | | | |
|---|---|---|---|
| 4,578,010 A | * | 3/1986 | Harigane et al. ............ 414/798 |
| 5,674,047 A | * | 10/1997 | Lapeus et al. ........ 414/798.1 X |
| 6,106,221 A | * | 8/2000 | Manuszak et al. ... 414/798.1 X |
| 6,283,703 B1 | * | 9/2001 | Dowling et al. ...... 414/798.1 X |

* cited by examiner

Primary Examiner—Janice L. Krizek
(74) Attorney, Agent, or Firm—Vierra Magen Marcus Harmon & DeNiro LLP

(57) ABSTRACT

A device for dispensing units of platform-loaded goods from a stack is provided which comprises a dispenser including a dispenser frame, capture blades, and a blade control. The capture blades retain the stack within the dispenser when in closed position and release the stack when in open position, and the blade control opens and closes the capture blades. The device also includes a device for engaging the dispenser such that the blade control is moved upwardly in relation to the dispenser frame to open said capture blades. A dispenser platform comprising a plurality of dispensers forming a dispenser assembly and a device for rotating the dispenser assembly, as well as an automated dispensing system for dispensing units of platform loaded goods comprising at least one dispenser, an engaging device for engaging each dispenser, a rotation device for rotating the engaging device, a lifting device for moving the engaging device vertically, and a control system for operating the rotation device and the lifting device, are also provided.

35 Claims, 16 Drawing Sheets

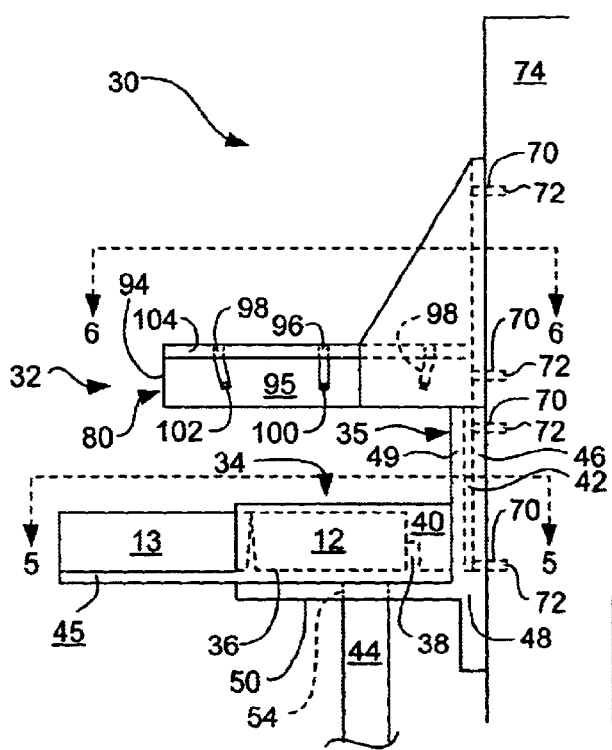
FIG. 4
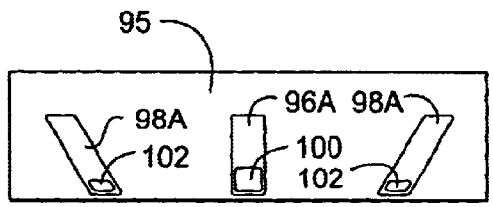
FIG. 4A
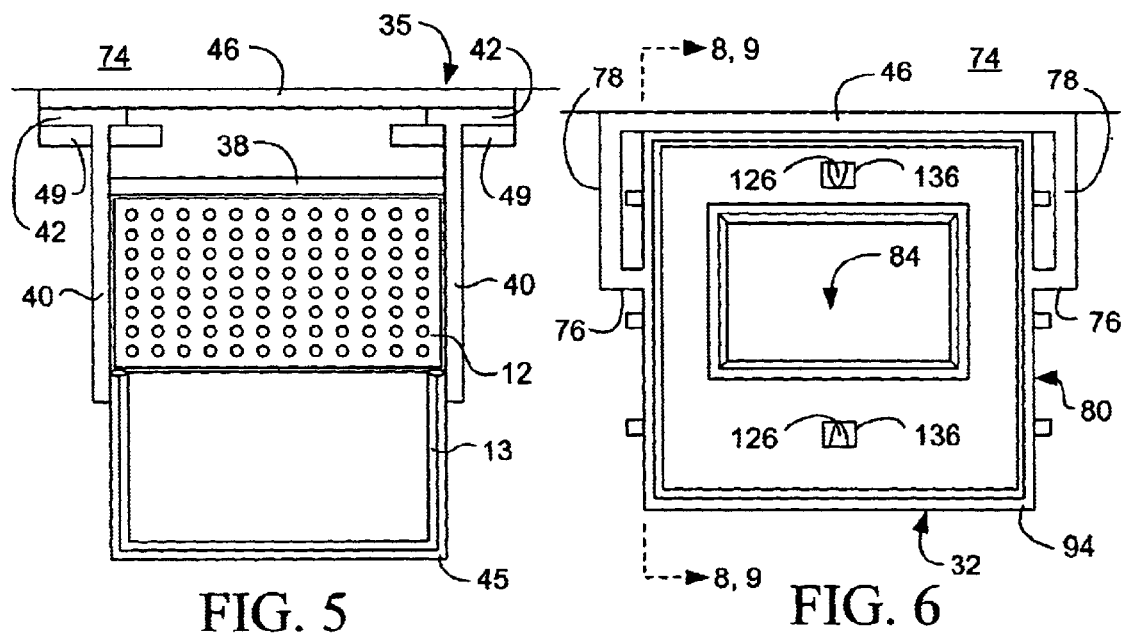
FIG. 5
FIG. 6

DISPENSING DEVICE FOR DISPENSING UNITS OF PLATFORM-LOADED GOODS

FIELD OF THE INVENTION

This invention relates generally to a device for dispensing units of platform-loaded goods from a stack of one or more units of platform-loaded goods onto a receptacle such as a rack.

BACKGROUND OF THE INVENTION

Many products on the market are sold loaded upon regularly-sized platforms. For example, pipette tips used for sample testing in laboratories are typically loaded into pipette tip flats so that the user need not handle the pipette tips individually. By utilizing platform loading, goods can be efficiently stored and transported in large quantities, as the platforms can be stacked and/or packaged one atop the other.

In many applications it is desirable to utilize a device which facilitates dispensing of platforms from a stack. For example, hand loading of pipette tip flats onto pipette tip racks is generally difficult and inefficient, as the pipette tip flat must be steadily maintained in parallel and aligned with the pipette tip rack for the pipette tips extending through the flat to register with and fit into the rack. Further, in applications where contamination of the goods loaded onto the platforms is a concern or where the goods are dangerous if handled by human operators, utilizing a device for unloading the platforms removes the risks of contamination and/or injury posed by human handling of the platforms.

A single laboratory or other facility utilizing such a dispensing aid will frequently use the same platforms to store goods of varying sizes and shapes. Accordingly, while dispensing devices are typically constructed to accommodate platforms of a predetermined size and shape, the dispensing device optimally will dispense those platforms when loaded with any size or shape of goods that allow the platforms to be stacked. Further, depending on the application desired, the user may wish to unload more than one platform from the dispensing aid at one time.

A number of devices have been developed that facilitate unloading pipette tip flats from a stack of pipette tip flats. U.S. Pat. Nos. 5,392,914 and 5,441,702 to Lemieux et al., and U.S. Pat. No. 5,779,984 to Kelly et al. each describe refill packs for pipette tip racks. The refill packs described in those patents enclose stacks of pipette tip flats in a box-like package having an open lower end from which the pipette tips in the lowest flat in the stack extend. The package is grasped by the user and the pipette tips in the lowermost flat are manually fitted into a pipette tip rack. The pipette tip flats are held within the rack by a flange extending around the perimeter of the open end of the refill pack. When the package is pressed downwardly, the flange is deformed outwardly by the downward force exerted by the lowermost pipette tip flat, and the flat is forced through the flange and remains on the rack. Once the flat has passed through the flange, the flange elastically returns to its original position, retaining the rest of the pipette tip flats within the package.

U.S. Pat. No. 5,470,538 to Lind describes a pipette tip rack loader ("the '538 loader") wherein a stack of pipette tip flats is loaded onto an upper platform which is spring biased to an elevated position and delivered to a pipette tip rack positioned on a stationary base below the upper platform. When the upper platform is depressed toward the pipette tip rack, slides supporting the stack of pipette tips retract, allowing the stack of pipette tips to fall onto the rack through the platform. As the upper platform is retracted to its upper position by the spring bias, the slides move inwardly to engage underneath the second pipette tip flat in the stack, leaving a single pipette tip flat on the rack.

U.S. Pat. No. 5,948,362 to Steinbrenner describes an apparatus for unloading stacked pipette tip flats ("the '362 apparatus"). The '362 apparatus includes a magazine which holds the pipette tip flats and utilizes an retaining element at its lower end which holds the pipette tip flats within the magazine except when the retaining element is activated to release the flats. The pipette tip flats are delivered onto a support such as an autoclave box with upraised flanges on either side. When the magazine is pressed down onto the autoclave box or the autoclave box is pressed upwardly against the magazine, the upraised flanges or edges of the autoclave box force the retaining element to move outwardly. In the various embodiments of the device, the height of the flanges, the positioning of vertical stops within the magazine limiting the insertion of the autoclave box, or the type of retaining element used is preselected such that for pipette tips of a desired size, only a single pipette tip flat will be dispensed when the retaining element is forced outwardly.

While the above-mentioned devices offer various advantages over the manual handling of pipette tip flats, there exists a continuing need for a reusable dispensing device which can dispense units of platform loaded goods of various sizes and shapes, can dispense one or more units of platform-loaded goods in a single dispensing action, and can be simply and reliably operated by an automated system processing the units of platform loaded goods.

Accordingly, it is an object of the present invention to provide a dispensing device which will dispense units of platform loaded goods of varying heights.

Another object of the present invention is to provide a dispensing device which will allow a user to deliver one or more units of platform loaded goods from a dispenser onto a receptacle in a single dispensing action.

A further object of the present invention is to provide a dispensing device which aligns platforms dispensed by the device with the receptacle to which they are delivered.

Other objects and advantages of the current invention will become apparent when the inventive platform loader is considered in conjunction with the accompanying drawings, specification, and claims.

SUMMARY OF THE INVENTION

A device for dispensing units of platform-loaded goods from a stack of one or more units of platform-loaded goods is provided which comprises a dispenser including a dispenser frame, capture blades, and blade control means. The dispenser frame forms a central aperture which defines a plane. The aperture has sufficiently large dimensions to allow passage of a units of platform-loaded goods therethrough when the unit is maintained in parallel with the plane. The capture blades retain the stack within the dispenser when they are in a closed position, and release the stack when they are in an open position such that units of platform-loaded goods in the stack can pass through the aperture. The blade control means opens and closes the capture blades, and is biased to hold the capture blades in the closed position.

The device also includes means for engaging the dispenser such that the blade control means are moved upwardly in relation to the dispenser frame to open the capture blades, allowing one or more units of platform loaded goods in the stack to fall through the aperture.

A dispenser platform for dispensing units of platform-loaded goods is further provided which comprises a plurality of dispensers forming a dispenser assembly, and means for rotating the dispenser assembly. Each dispenser includes a dispenser frame forming a central aperture, capture blades for retaining a stack of units of platform-loaded goods within the dispenser when the capture blades are in a closed position and for releasing the stack when in an open position such that one or more units of platform-loaded goods in the stack can pass through the aperture, and blade control means for opening and closing the capture blades. The blade control means are biased to hold the capture blades in the closed position. The plurality of dispensers are positioned within the dispenser assembly such that at least one region of the dispenser assembly is defined wherein when the dispenser assembly is rotated each dispenser in the assembly may successively be positioned within the region and activated to release one or more units of platform-loaded goods.

An automated dispensing system for dispensing units of platform loaded goods is also provided, which comprises at least one dispenser, engaging means for engaging each dispenser, means for moving the engaging means, lifting means for moving the engaging means vertically, and a control system for operating the rotation means and lifting means. Each dispenser used in the automated dispensing system includes a dispenser frame forming a central aperture, capture blades for retaining a stack of the units of platform-loaded goods within the dispenser when in a closed position and for releasing the stack when in an open position such that one or more units of platform-loaded goods in the stack can pass through the aperture, and blade control means for opening and closing the capture blades which are biased to hold the capture blades in the closed position.

The engaging means are capable of engaging each dispenser such that its blade control means are moved upwardly in relation to its dispenser frame to open its capture blades, allowing one or more units of platform-loaded goods in its stack to fall through its aperture. The means for moving the engaging means moves the engaging means over a first range, such that within the first range the engaging means can be positioned with respect to at least one dispenser such that if it is raised it will engage the dispenser, and such that the engaging means also can be positioned at a delivery site. The lifting means are operable to move the engaging means vertically over a second range, such that within the second range the engaging means can be moved into and out of engagement with the at least one dispenser.

BRIEF DESCRIPTION OF THE DRAWINGS

FIG. 4 is a side view of the inventive dispensing device of FIG. 3.

FIG. 4A is a side view of the exterior of one side of the frame of the platform engaging and releasing structure.

FIG. 5 is a top plan view of the garage of the inventive dispensing device of FIG. 4 taken at section line 5—5.

FIG. 6 is a top plan view of the dispenser of the inventive dispensing device of FIG. 4 taken at section line 6—6.

DESCRIPTION OF THE PREFERRED EMBODIMENT

Figure 1:
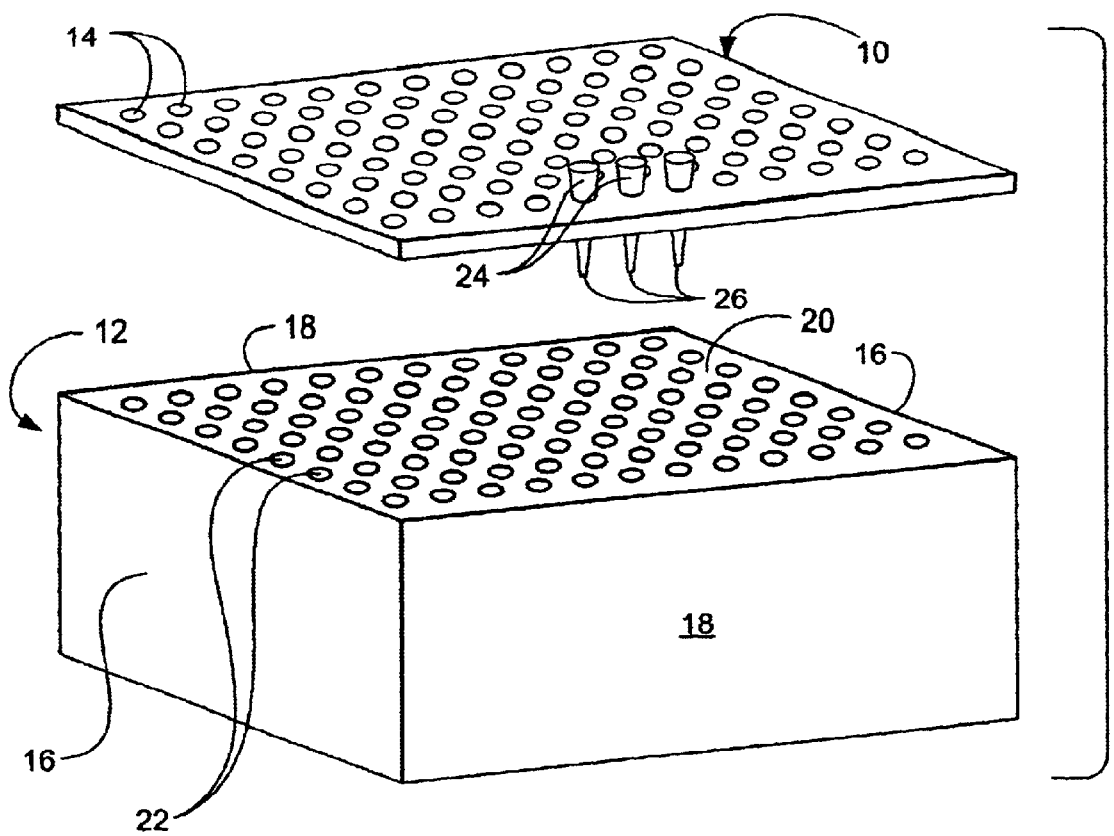
FIG. 1 is an exploded perspective view of a standard pipette tip flat and pipette tip rack which may be utilized in conjunction with the inventive device.
Figure 2:
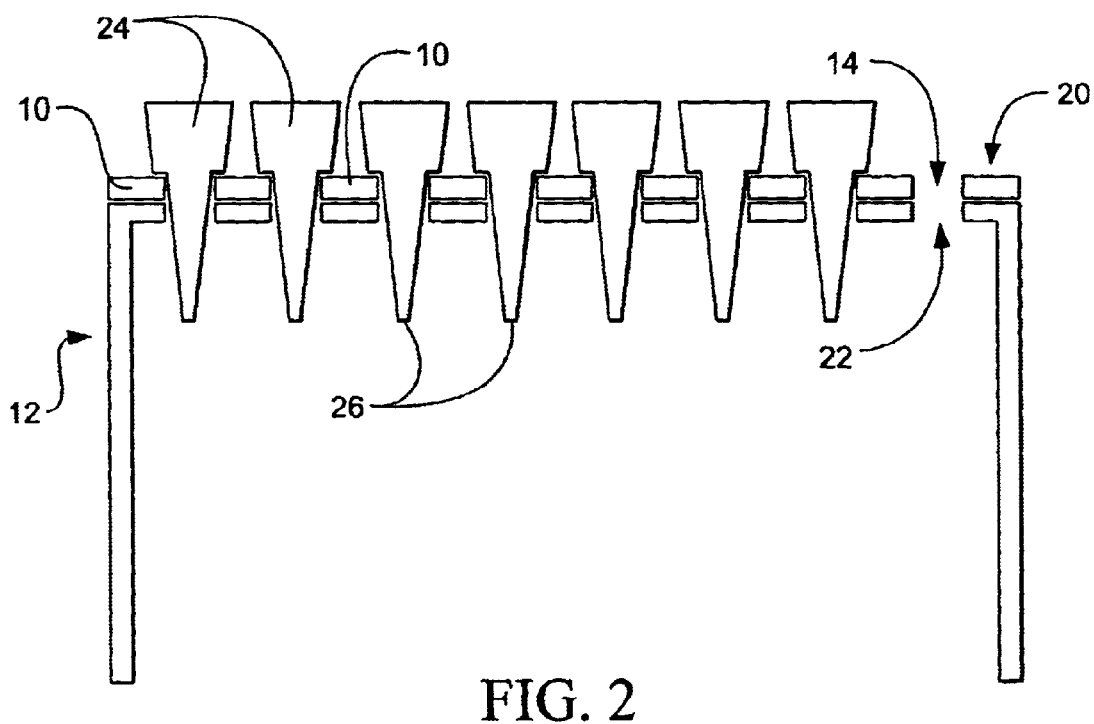
FIG. 2 is a side cross-sectional view of a standard pipette tip flat atop the standard pipette tip rack of FIG. 1.

The inventive dispensing device may be used to successively deliver units of platform-loaded goods from a stack of one or more units of platform-loaded goods onto a receptacle. In the described embodiments of the inventive device, it is assumed that the units of platform-loaded goods dispensed by the inventive device are pipette tip flats. In those embodiments which are designed for manual use, it is further assumed that the pipette tip flats are delivered onto a pipette tip rack. For reference, a typical pipette tip flat 10 and pipette tip rack 12 are shown in FIGS. 1 and 2. Flat 10 is rectangular and forms 96 apertures 14 in an 8×12 array. Preferred rack 12 comprises side walls 16 and 18 and a rectangular upper surface 20 which forms 96 apertures 22. Apertures 22 align with apertures 14 when flat 10 is positioned atop surface 20. When flat 10 is in use, pipette tips 24 are fitted through apertures 14 of flat 10 such that the pipette tip ends 26 extend below apertures 14. When flat 10 is loaded with pipette tips 24, it may be delivered atop rack 12 by aligning the tip ends 26 with apertures 22 of the rack 12 and then lowering flat 10 until it rests upon upper surface 20, with pipette tips 24 passing through both apertures 14 and 22.

In the embodiments of the inventive device designed for automated use, it is assumed that the pipette tip flats are delivered either onto a pipette tip rack 12 or onto a robotic gripper, which will be described in detail below. However, it should be understood that for any of the described embodiments, both manual and automated, the inventive device can be used to process pipette tip flats housing any number of pipette tips of any size in any spatial configuration. Further, the described embodiments may be used to process units of any platform-loaded goods, and not only pipette tip flats. In this regard, the term "units of platform-loaded goods" includes both platforms upon which goods of any sort are loaded, as well as goods which themselves constitute platforms, such as microplates, or microplate lids.

Figure 3:
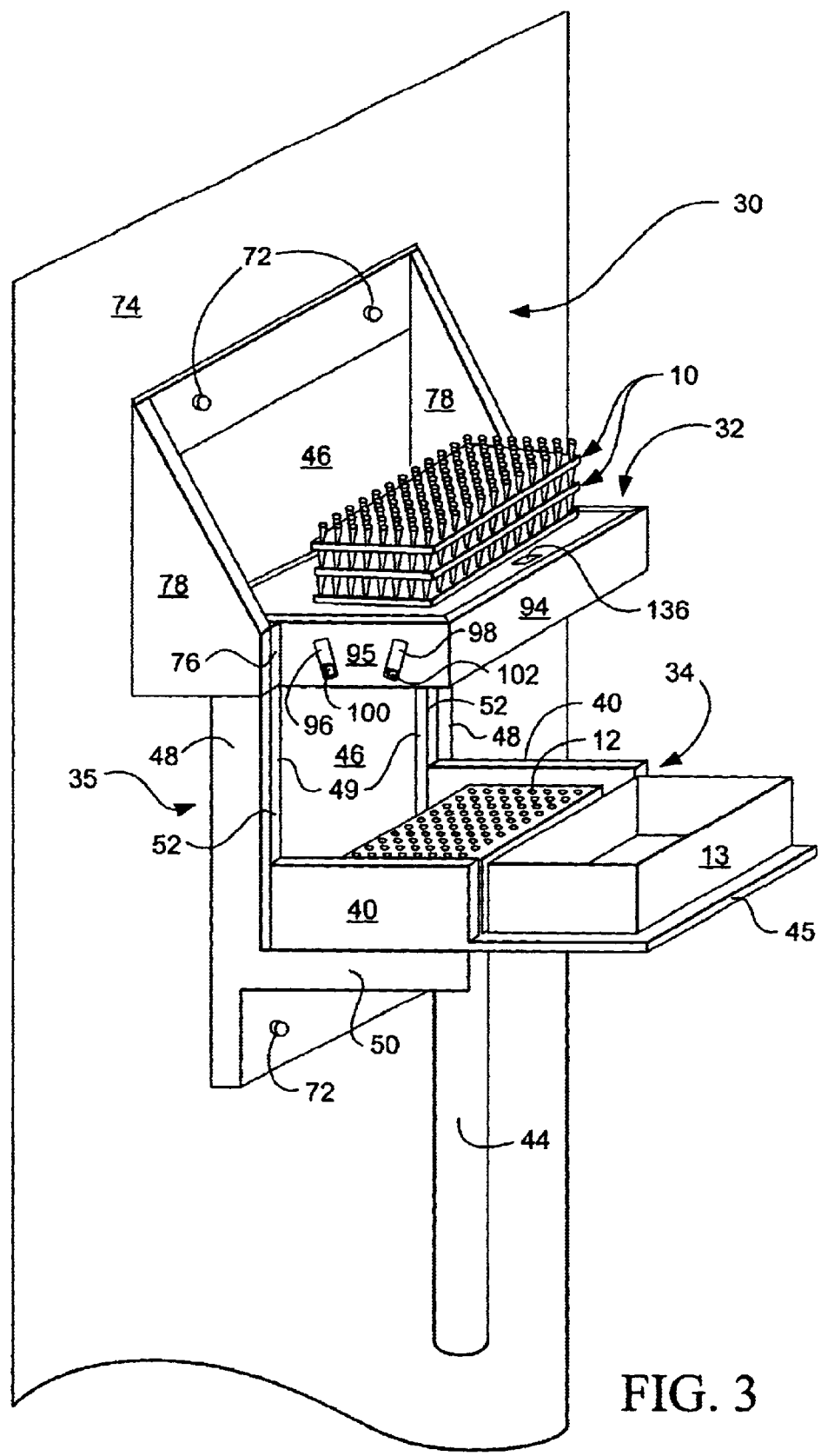
FIG. 3 is a perspective view of a preferred embodiment of the inventive dispensing device.

Referring to FIGS. 3 and 4, a preferred embodiment 30 of the inventive platform dispensing device which is particularly suitable for manual operation is shown. Device 30 primarily comprises a dispenser 32 and a garage 34. Dispenser 32 holds one or more stacked pipette tip flats 10 as shown in FIG. 3 and, upon activation, will deliver the lowermost flat 10 onto a pipette tip rack 12 housed within garage 34. Dispenser 32 and garage 34 are preferably connected to a housing 35 which aligns garage 34 with dispenser 32 for efficient use.

Referring to FIGS. 3 and 4, garage 34 preferably comprises a base 36, a back stop 38, two side walls 40, tongues 42, and a lifting member 44. Garage 34 is open at the top such that when a receptacle, such as pipette tip rack 12, is placed within the garage 34, no structures impede access to the upper surface of the receptacle. While garage 34 can include a front wall, garage 34 is preferably left open at the front for easier placement of the receptacle into the garage 34. The width of back stop 38 and length of side walls 40 should be chosen such that a receptacle of the desired size to receive platforms loaded into the dispenser 32 may be received within garage 34. Lifting member 44 is preferably included to provide a convenient means for lifting garage 34 within housing 35 by applying a single upward force to lifting member 44 from a position below the housing 35. Accordingly, if the device 30 is used manually, the garage 34 may be lifted using only one hand, for convenience, while in an automated system, an upward force need only be applied below lifting member 44 to lift garage 34. Base 36 of garage 34 may be made longer than side walls 40 such that base 36 forms a forwardly extending lip 45. Lip 45 is preferably provided for supporting any structures connected to or extending from the receptacle inserted into garage 34 to receive a pipette tip flat 10, such as a lid 13 hingedly connected to pipette tip rack 12.

Housing 35 preferably utilizes a vertical linear slide to align garage 34 within housing 35. Referring to FIGS. 3 through 5, the vertical linear slide depicted comprises grooves 52 in housing 35 working in conjunction with tongues 42 of garage 34, as further described below. As shown, housing 35 preferably comprises a back wall 46, side walls 48, panels 49 inwardly extending from side walls 48 and spaced apart from back wall 46, and a base 50. As shown in FIG. 3, panels 49 each preferably form a vertically oriented groove 52 through which a side wall 40 of the garage 34 extends. As shown in FIGS. 4 and 5, the tongues 42 of the garage 34 are fitted between panels 49 and back wall 46, holding garage 34 in alignment with housing 35 and allowing for vertical movement of garage 34 within housing 35 as side walls 40 slide within grooves 52. Each groove 52 should extend vertically to a sufficiently elevated position such that the garage 34 may be raised to the top of housing 35 to contact dispenser 32 as will be described below. Referring to FIG. 4, base 50 incorporates an aperture 54 through which lifting member 44 of garage 34 extends.

Device 30 as shown is designed to be wall-mounted, as wall mounting is particularly useful in laboratory work where conservation of countertop space is highly desirable. Referring to FIGS. 3 and 4, apertures 70 may be made in rear wall 46 of housing 35 through which fasteners such as screws 72 may be used to fasten housing 35 to a wall 74. However, it should be understood that device 30 may easily be adapted to be a stand-alone device in a variety of ways, including but not limited to modifying housing 35 to include a secondary lower base below base 50 and lifting member 44 which would rest on a supporting surface such as a table or counter, or removing lifting member 44 and fastening base 50 to a supporting surface.

Dispenser 32 is positioned above garage 34 within housing 35. Dispenser 32 may be attached to housing 35 using fasteners or the like, or may be formed integrally therewith. As shown in FIGS. 3 and 6, dispenser 32 is mounted in the upper portion of housing 35. The rear portion of the dispenser 32 is. fixed to or formed with the back wall 46 of the housing 35, and inwardly extending flanges 76 on upper side walls 78 of housing 35 are fastened or formed with the sides of dispenser 32.

Figure 7:
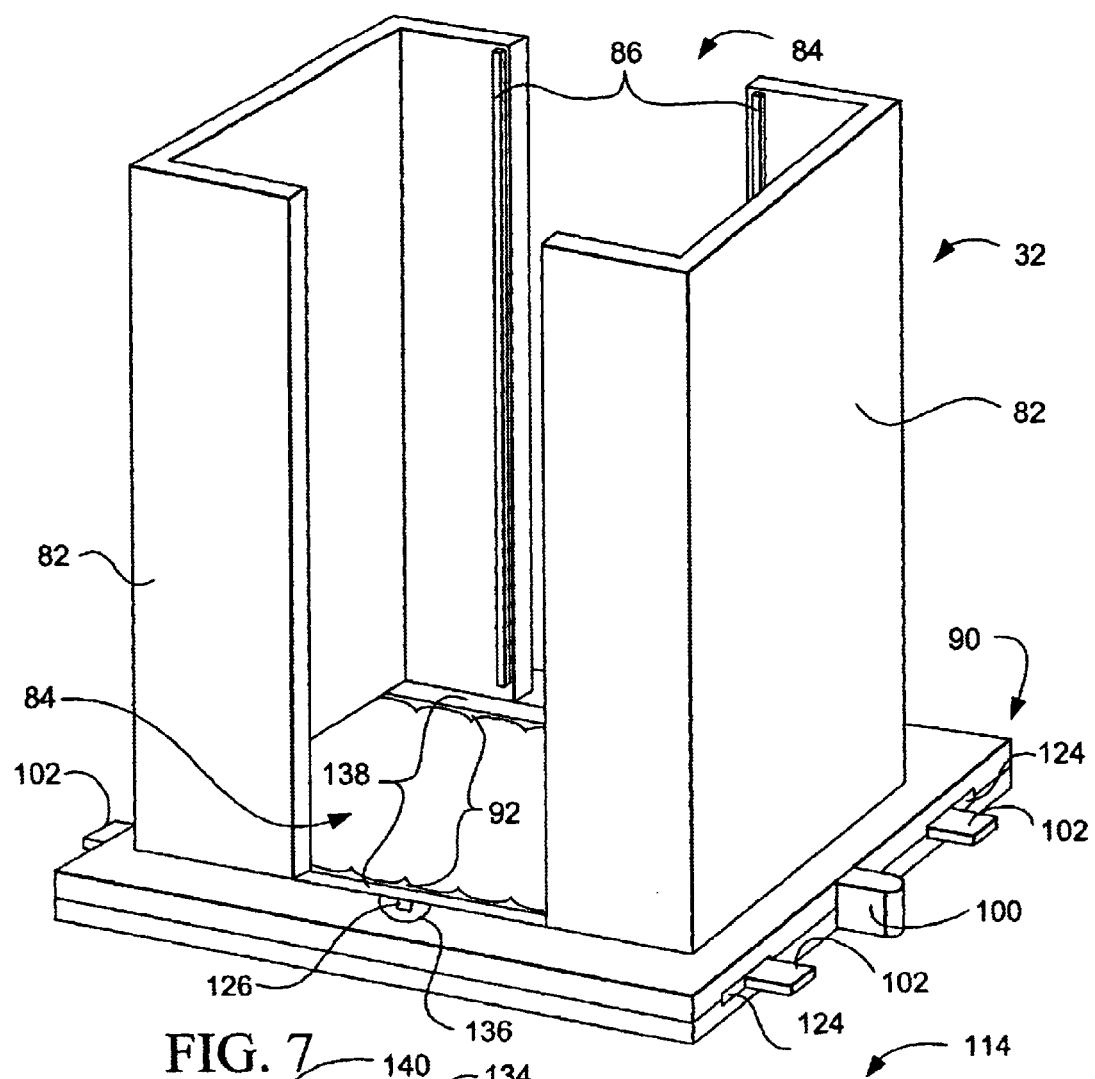
FIG. 7 is a perspective view of the inner portion of the dispenser of FIGS. 3 and 4 with guides positioned atop the inner portion.

Dispenser 32 primarily comprises a platform engaging and releasing structure 80, described in detail below. Referring to FIG. 7, dispenser 32 may also include guides 82 (not shown in FIG. 3 or 6 for clarity of illustration) for aligning and holding pipette tip flats 10 stacked within dispenser 32. If used, guides 82 preferably have a vertical height equal to that of the stack of flats 10 deposited into dispenser 32. Access channels 84 formed between guides 82 facilitate depositing platforms into the dispenser by accommodating the entry of the user's hand. For example, should pipette tip flats in a typical package of flats (not shown) be loaded into the dispenser 32, access channels 84 allow the user to remove safety ties preventing the flats from escaping the packaging in order to release the flats into the dispenser 32. Alternatively, if the device 30 is used in an automated system, access channels 84 would accommodate the insertion of a robotic device (not shown) loading the flats 10 into the dispenser 32. Runners 86 may be fitted within guides 82, such as at the edges of guides 32 proximate to channels 84, to help guide flats 10 delivered into dispenser 32 into proper alignment with the platform engaging and releasing structure 80. To prevent accidental movement of the guides 82 in relation to the inner portion 90 of the structure 80, stabilizing means may be added to the inventive device. For example, if the device is table mounted, the structure 80 may incorporate features such as ridges or slots (not shown) which support the guides 82 in the desired position.

Figure 8A:
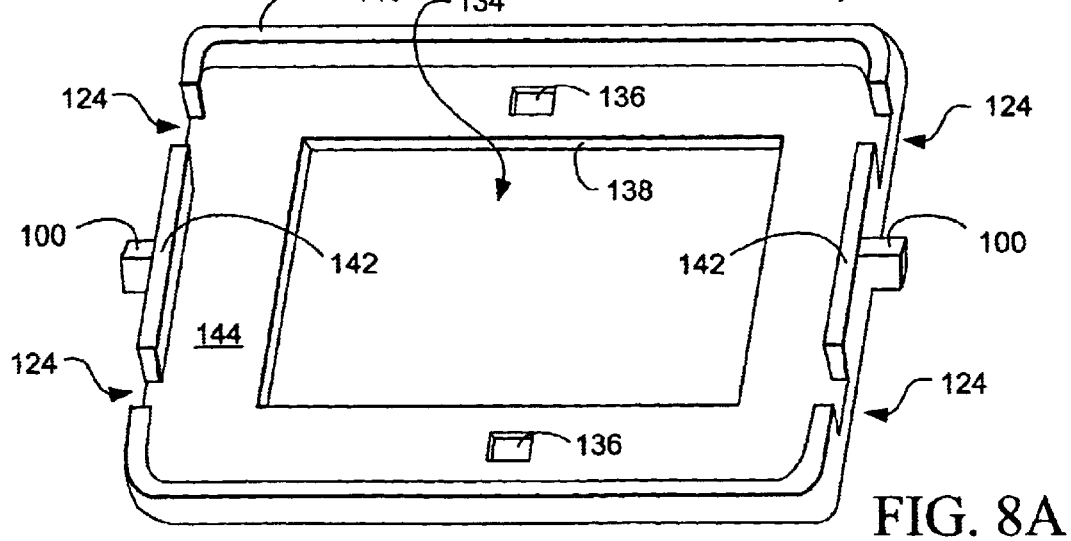
FIG. 8A is a perspective view of the underside of a top portion of the platform engaging and releasing structure used in the dispenser.
Figure 8:
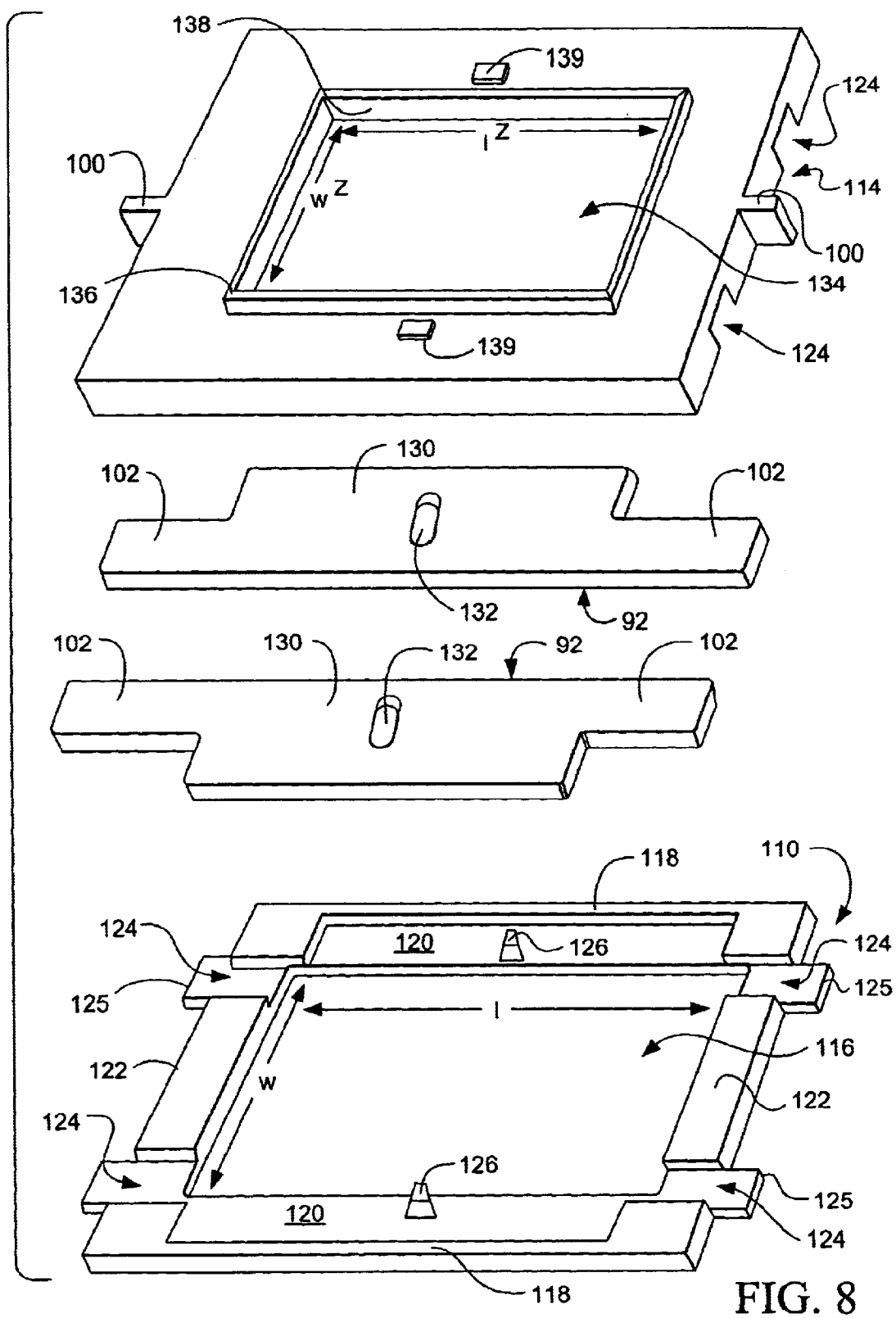
FIG. 8 is an exploded perspective view of the inner portion of a platform engaging and releasing structure used in the dispenser.

The inner portion 90 of platform engaging and releasing structure 80 is shown in constructed form in FIG. 7 and in disassembled form in FIG. 8. Platform engaging and releasing structure 80 is designed such that, in its natural position, pipette tip flats loaded into the structure 80 rest upon capture blades 92 extending into the interior of structure 80, while in an activated position, capture blades 92 retract to allow one or more of the flats to fall through structure 80 and onto a pipette tip rack positioned below structure 80 within garage 34. Capture blades 92 each form two blade ends 102.

The construction of platform engaging and releasing structure 80 may be accomplished as follows.

FIGS. 3, 4, and 6 show the frame 94 of platform engaging and releasing structure 80 which encloses the inner portion 90 (shown in FIGS. 8 and 9) of the structure 80. Referring to FIG. 4, each of the outer sides 95 of frame 94 forms three slots: a center slot 96 and two angled camming slots 98. As shown, on one or both sides 95 slots 96 and 98 may extend up to the upper edge of the side 95 to allow for the easy insertion or removal of post 100 and blade ends 102 into slots 96 and 98, respectively, during assembly or disassembly of the device, in which case a stopper piece 104 is later fitted over the upper portion of side 95 to prevent post 100 and blade ends 102 from exiting slots 96 and 98 during operation of the device. Preferably the extended slots 96 and 98 and stopper piece 104 are used on one side 95 of the frame 94 while the other side 95 forms closed slots 96A and 98A as shown in FIG. 4A. However, it should be understood that closed slots may be used on both sides 95 if desired.

Referring to FIG. 8, inner portion 90 comprises a base 110, capture blades 92, and a top 114. Base 110 is generally formed in the shape of a rectangular ring forming a central rectangular aperture 116. Aperture 116 should have sufficient length 1 and width w to accommodate the passage of a pipette tip flat 10 therethrough when the flat 10 is aligned in parallel with base 110. While the bottom of base 110 (not shown) is substantially flat, the upper side of base 110 forms a number of structures which are designed to enclose capture blades 92 when base 110 is aligned with top 114. Along the longer outer sides of base 110, two U-shaped edges 118 are formed, from which the floor 120 of the base 110 extends inwardly. Lips 125 of floor 120 are formed which extend outwardly a small distance from the outer edges of edges 118 and members 122 at apertures 124. Rectangular members 122 are formed in the center portion of the shorter sides of base 110 such that four apertures 124 are formed between the ends of U-shaped edges 118 and members 122. Posts 126, extending higher than U-shaped edges 118 and members 122, are formed at the midline of the longer sides of the base 110 towards the inner edge of aperture 116.

Capture blades 92 each form a wider middle portion 130 defining the two blade ends 102. A slot 132 is formed in the center of each capture blade 92 such that the slot 132 may be fitted over one of the posts 126 of the base 110 such that the middle portion 130 of the capture blade slidably rests upon the floor 120 of the base 110 and the blade ends 102 rest within apertures 124. Each slot 132 is preferably shaped to have a width just sufficient to accommodate the entry of the corresponding post 126 and a length longer than that of the corresponding post, such that the capture blades 92 can slide inwardly and outwardly within the interior portion 90 while the posts 126 are engaged within slots 132. Apertures 124 should be sufficiently wide in relation to blade ends 102 that edges 118 and rectangular members 122 will not impede capture blades 92 from sliding inwardly and outwardly fully as allowed by slots 132.

Top 114, shown in FIGS. 8 and 8A, is, like base 110, generally rectangular, and forms a central rectangular aperture 134. Referring to FIG. 8, which depicts the upper surface of top 114, aperture 134, like aperture 116, should have sufficient length 12 and width w2 to accommodate the passage of a pipette tip flat therethrough when the flat is aligned in parallel with the top 114. A upright ridge 136 may be provided which surrounds aperture 134 and which may provide support for guides 82. The inner edge 138 of the ridge 136 preferably slopes inwardly and downwardly to assist in guiding pipette tip flats loaded into the dispenser 32 into aperture 134 in the proper orientation. Top 114 forms two further apertures 139 in the center of each of its side walls near its interior edge to accommodate posts 126 of base.

Referring to FIG. 8A, the underside of top 114 is formed having two U-shaped edges 140 along its longer sides, and members 142 centered along its shorter sides such that apertures 124 are further formed between the ends of U-shaped edges 140 and members 142. Posts 100 are formed on members 142 extending outwardly from the sides of top 114. Edges 140 and members 142 extend upwardly from the floor 144 of the underside of top 114 by a height which is approximately equal to the thickness of edges 118 and members 122 of base 110.

Referring to FIGS. 8 and 8A, when the inner portion 90 is assembled, capture blades 92 are positioned a top base 110 with posts 126 fitting through slots 132. Top 114 is then secured over base 110, sandwiching capture blades 92 between top 114 and base 110. Top 114 is made both slightly longer and wider than base 110 such that when top 114 is secured over base 110, U-shaped edges 118 of base 110 are inwardly adjacent to U-shaped edges 140 of top 114, rectangular members 122 of base 110 are inwardly adjacent to members 142 of top 114, and the edges of lips 125 are flush with the outer edges of members 142 and edges 140. As edges 140 and members 142 have a height approximately equal to the thickness of edges 118 and members 142 of base 110, the lower surface of edges 140 and members 142 will be flush with the lower surface of base 110 when the inner portion 90 is assembled. Capture blades 92 are made sufficiently thin such that the vertical spacing left between floors 120 and 144 when the top 114 and base 110 are secured together is such that the blades 92 may slide horizontally without excessive friction with base 110 and top 114.

Accordingly, when constructed, the inner portion 90 of platform engaging and releasing structure 80 constitutes a generally rectangular structure forming a rectangular central aperture and sandwiches capture blades 92 such that the capture blades can slide outwardly until they extend into the rectangular central aperture, as shown in FIG. 7, or be retracted into the structure 80 to leave the aperture open, by moving blade ends 102 within apertures 124. When the device 30 is fully assembled, inner portion 90 is fitted into frame 94 by fitting posts 100 into slots 96 and blade ends 102 into angled camming slots 98. Apertures 124 should be positioned such that when the inner portion 90 is fitted into frame 94 and the force of gravity causes blade ends 102 to slide downwardly to the lowest position within camming slots 98, blade ends 102 are in the inwardmost position within apertures 124, such that capture blades 92 extend fully into the central rectangular aperture.

Figure 9:
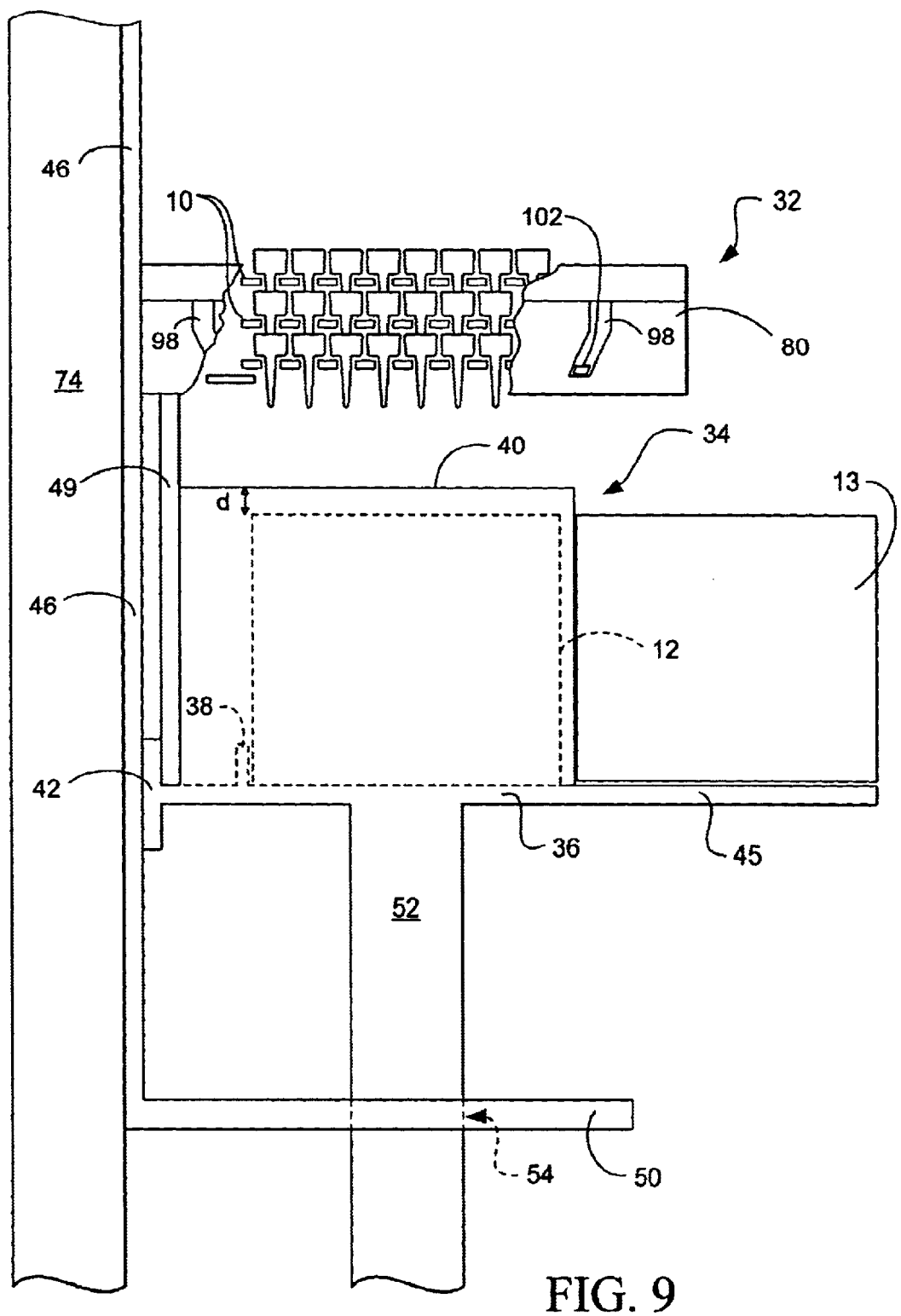
FIG. 9 is a side view of the inventive dispensing device wherein the garage of the device is being lifted towards the dispenser of the device.
Figure 10:
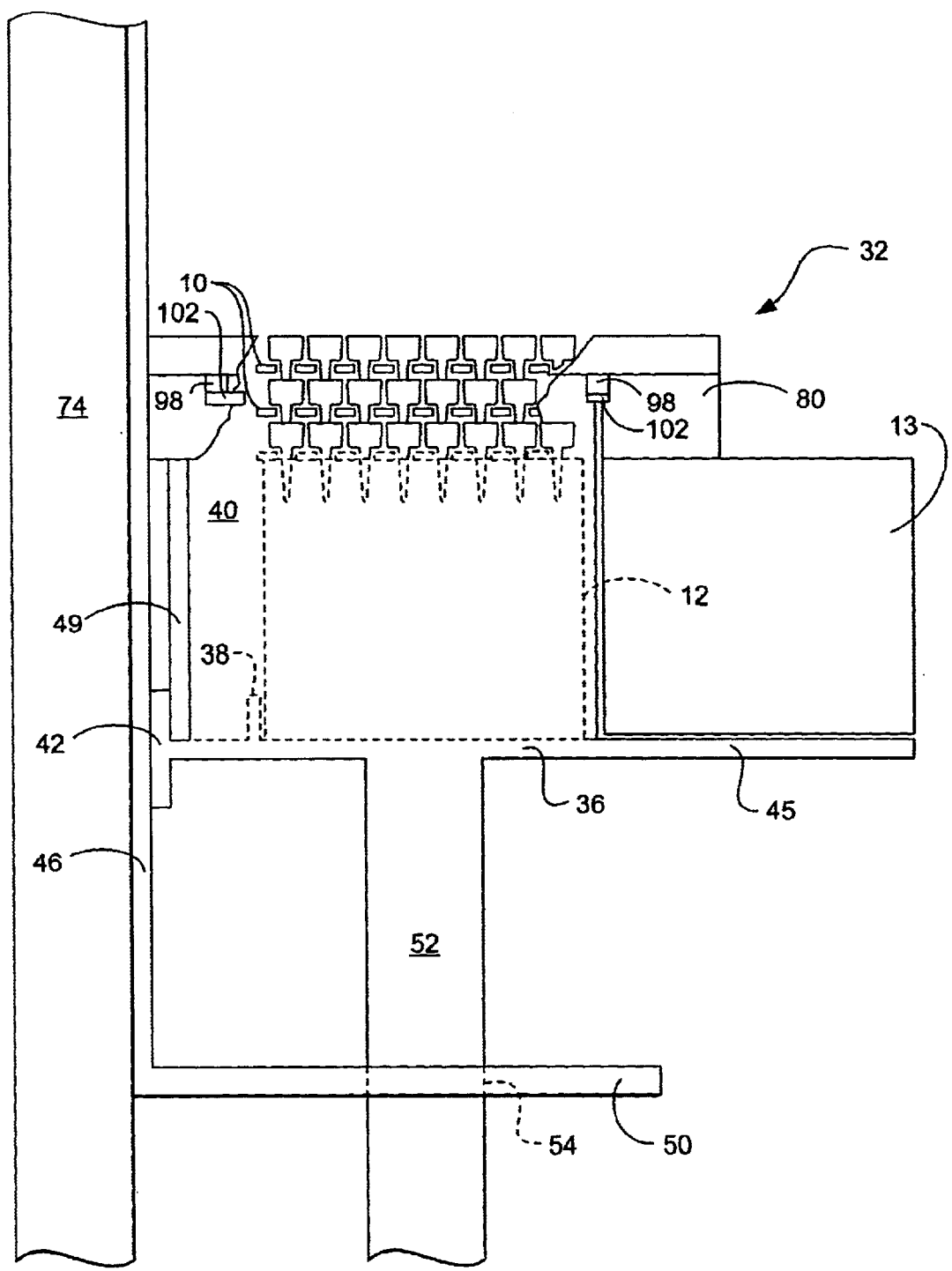
FIG. 10 is a side view of the inventive dispensing device wherein the garage of the device has lifted and opened the capture blades of the dispenser.

FIGS. 9 and 10 depict the structure of the platform dispensing device 30 in operation. Pipette tip rack 12 is positioned within garage 34 and garage 34 is lifted towards dispenser 32, for example, by using lifting member 44. Garage 34 is maintained by tongues 42 and the grooves 52 in panels 49 of housing 35 in position such that the side walls 40 of garage 34 register with blade ends 102 of capture blades 92 (not shown). Back stop 38 of garage 34 is positioned such that when rack 12 is placed adjacent to back stop 38, rack 12 is aligned with flats 10 loaded into dispenser 32.

As shown in FIG. 9, prior to contact of walls 40 of garage 34 with blade ends 102, blade ends 102, due to the force of gravity, remain at the bottom of camming slots 98, and thus maintain capture blades 92 in their closed position, retaining flats 10 within the dispenser 32. However, as shown in FIG. 10, as garage 34 is lifted, walls 40 push blade ends 102 upward within camming slots 98, thereby lifting the inner portion 90 (see FIG. 7) of the platform engaging and releasing structure 80, as well as guides 82 (see FIG. 7) and the stack of pipette tip flats 10. The upward and outward angling of camming slots 98 forces blade ends 102 outwardly within apertures 124 (see FIGS. 7 and 8), which causes capture blades 92 to retract into structure 80. This pulls capture blades 92 out from underneath the lowermost flat 10 and allows flat 10 to fall onto rack 12, as shown in FIG. 10. When garage 34 is then lowered, blade ends 102 lower again within camming slots 98 due to the force of gravity created by the weight of inner portion 90 and guides 82 (see FIG. 7), thereby closing capture blades 92 underneath the next flat 10 of pipette tips and retaining the next flat 10 of pipette tips within dispenser 32. Posts 100 (see FIGS. 3 and 4), which fit into slots 96 (see FIG. 4), maintain the inner portion 90 (see FIG. 7) of platform engaging and releasing structure 80 in parallel alignment with frame 94 as inner portion 90 is raised and lowered.

Referring to FIGS. 9 and 10, by making the height difference d between the height of the garage walls 40 and the height of the rack 12 very small, the device 30 will deliver only a single flat 10 even where the pipette tips 24 are very small and accordingly the height difference between the flats 10 in the stack is very small. This occurs because, as the garage walls 40, rather than the rack 12, activate the opening and closure of capture blades 92, the flat 10 delivered to the rack 12 will fall by approximately distance d onto the rack 12, bringing the stack of flats downwardly by only distance d. This brings the delivered flat 10 below capture blades 92 while retaining the next flat 10 above capture blades 92 as long as the distance between the flats 10 in the stack is not less than distance d. As soon as the garage 34 is lowered, the capture blades immediately close, thus ensuring that only one flat 10 is delivered to the rack 12. Racks of differing heights can be used within garage 34 while maintaining a small distance d by making the garage height large enough to accommodate large racks and inserting a block or the like (not shown) under small racks to raise the small racks in relation to walls 40.

Similarly, where the platforms delivered by the device 30 will not be harmed or misaligned by a fall over a larger distance d, more than one platform may be delivered onto a receptacle placed within the garage 34 by increasing the distance d between the height of walls 40 and the upper surface of the receptacle.

Referring to FIGS. 3 and 4, because garage 34 is held in a defined relation to dispenser 32 by housing 35, garage 34 cannot become misaligned with blade ends 102, and accordingly the inner portion 90 (see FIG. 7) of structure 80 will always be raised evenly such that flats 10 falling through the central aperture will be properly aligned with the rack 12 housed in the garage 34.

Figure 11:
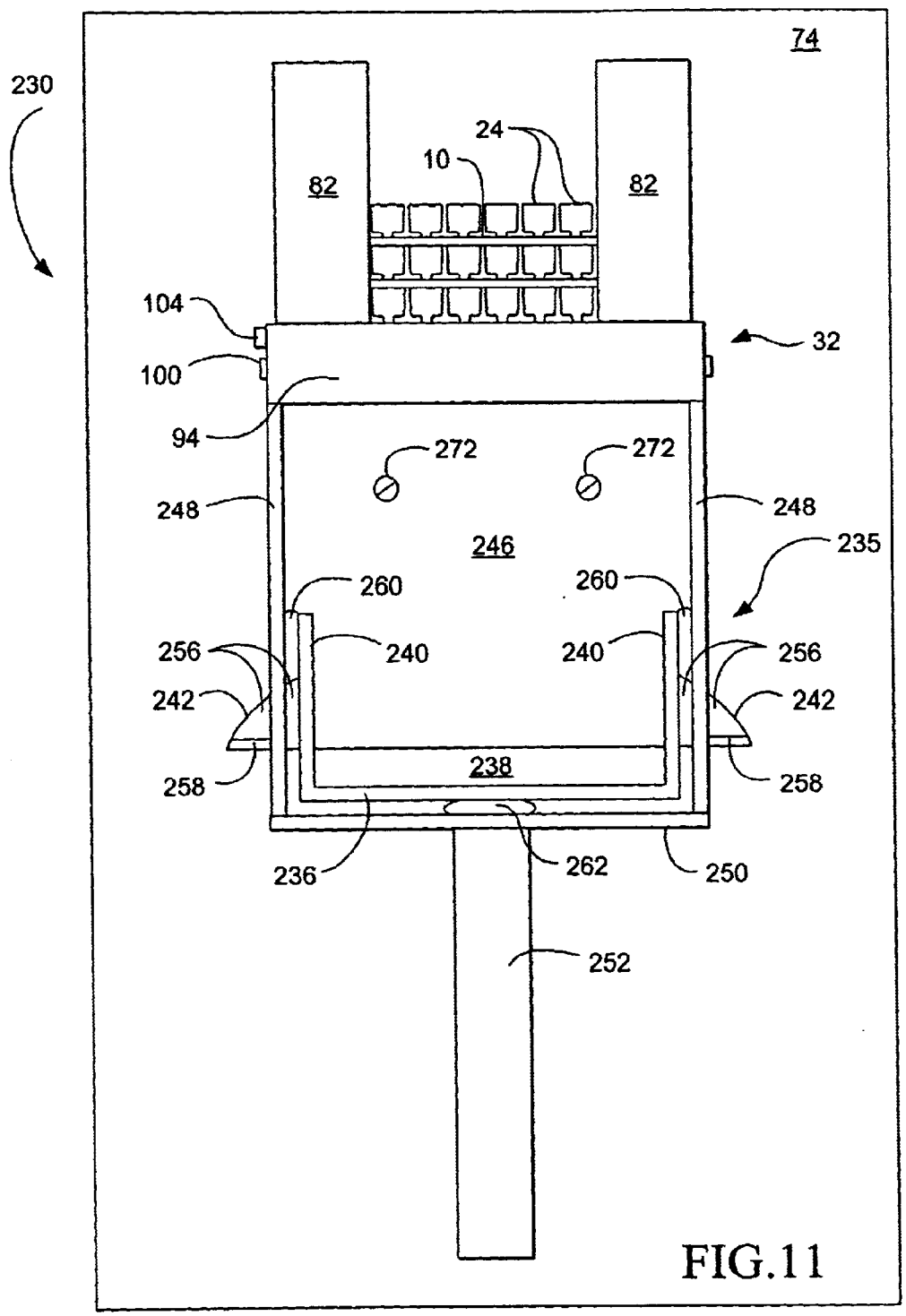
FIG. 11 is a front view of an alternative embodiment of the inventive device.
Figure 12:
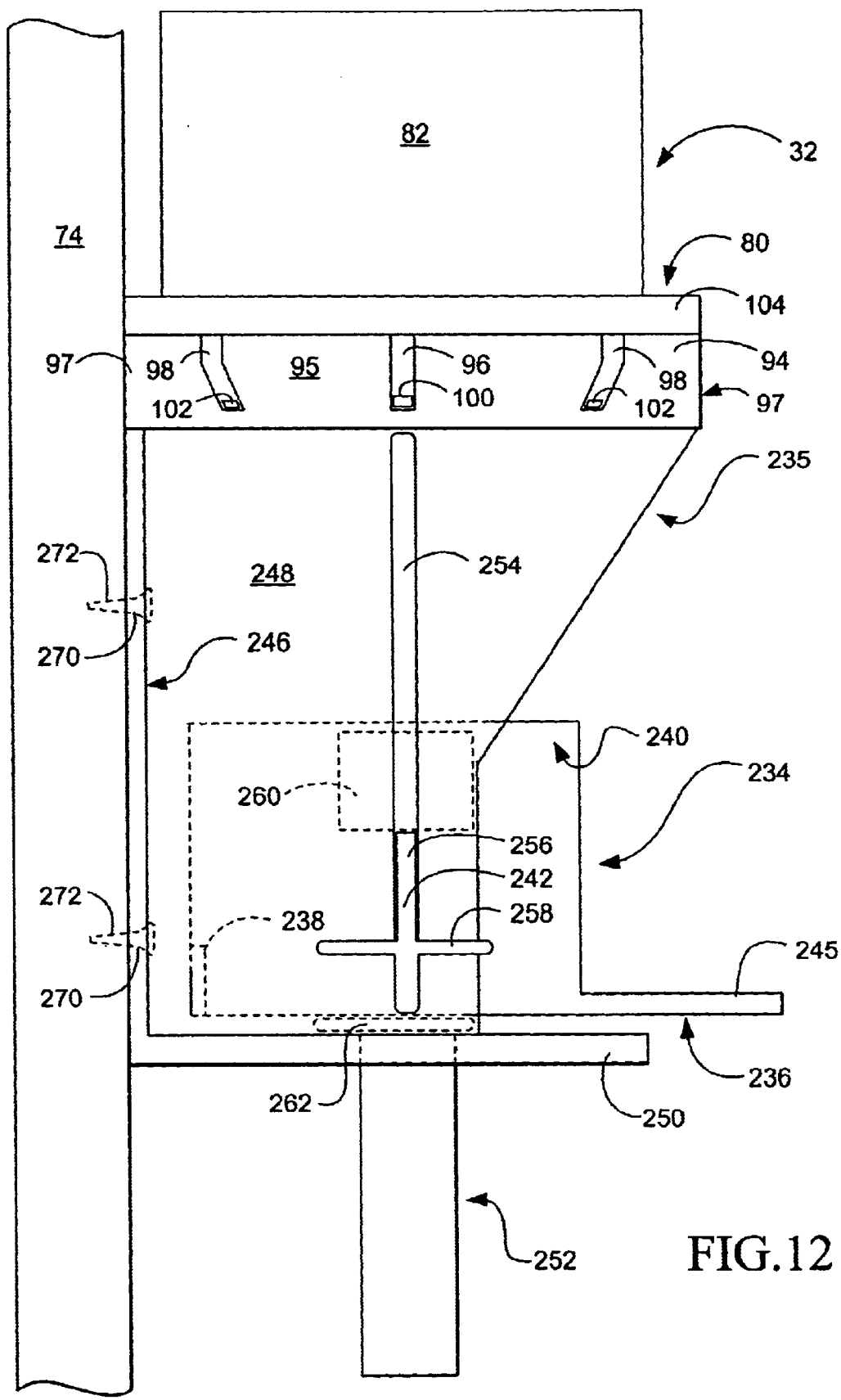
FIG. 12 is a side view of the alternative embodiment of FIG. 11.

FIGS. 11 and 12 depict an alternative embodiment 230 of the inventive platform dispensing device. Device 230 comprises dispenser 32, an alternative garage 234, and an alternative housing 235. The dispenser 32 used with device 230 may be identical to the dispenser used with device 30.

Alternative garage 234 and housing 235 differ from garage 34 and housing 35 of device 30 primarily in that they employ different structures to maintain the alignment between garage 234 and housing 235, and secondarily in that the lifting means 252 provided to raise and lower garage 234 is not attached to garage 234.

Alternative garage 234 comprises a base 236, a back stop 238, two side walls 240, and two hand grips 242 extending outwardly from side walls 240. In similar fashion to garage 34, base 236 of garage 234 is made longer than side walls 240 such that base 236 forms forwardly extending lip 245 for supporting structures inserted into garage 234, such as the lid of a pipette tip rack.

Hand grips 242 are preferably included to accomplish several functions: First, grips 242 provide an alternative, convenient means for a user to lift garage 234; and second, grips 242 properly align garage 234 within housing 235. Housing 235 preferably comprises a back wall 246, two side walls 248, a base 250, and lifting member 252, which extends through base 250. As shown in FIG. 12 for one side wall 248 and one grip 242, side walls 248 each preferably form a vertically oriented alignment slot 254 through which a vertically oriented arm 256 of the corresponding grip 242 extends. As shown in FIGS. 11 and 12, the portion of the arm 256 of each grip 242 which extends outside the wall 248 of housing 235 forms an outwardly flaring flange 258 which provides a convenient lifting surface for a user and which prevents arm 256 from sliding inwardly through alignment slot 254. On the interior of housing 235, each grip 242 forms an upper stop 260 above arm 256 which is wider than alignment slot 254 such that grip 242 similarly cannot slide outwardly through alignment slot 254. Each alignment slot 254 extends vertically along nearly the full length of side walls 248 such that the garage 234 may be raised to the top of housing 235 by sliding arms 256 of grips 242 upwardly through the alignment slots 254.

Lifting member 252, which is fitted through an aperture in base 250, forms a head 262 which has a larger diameter than the aperture such that it cannot pass therethrough. Head 262 forms a flat upper surface upon which the base 236 of garage 234 rests. When an upward force is exerted upon lifting member 252, head 262 engages the underside of garage 234 and lifts garage 234.

Like device 30, device 230 may be wall mounted, as shown in FIGS. 11 and 12, or adapted to be mounted upon another structure, such as on a table or counter. To facilitate wall mounting of the device 230, apertures 270 may be made in rear wall 246 of housing 235 through which fasteners such as screws 272 may be used to fasten housing 235 to the wall 74.

Figure 13:
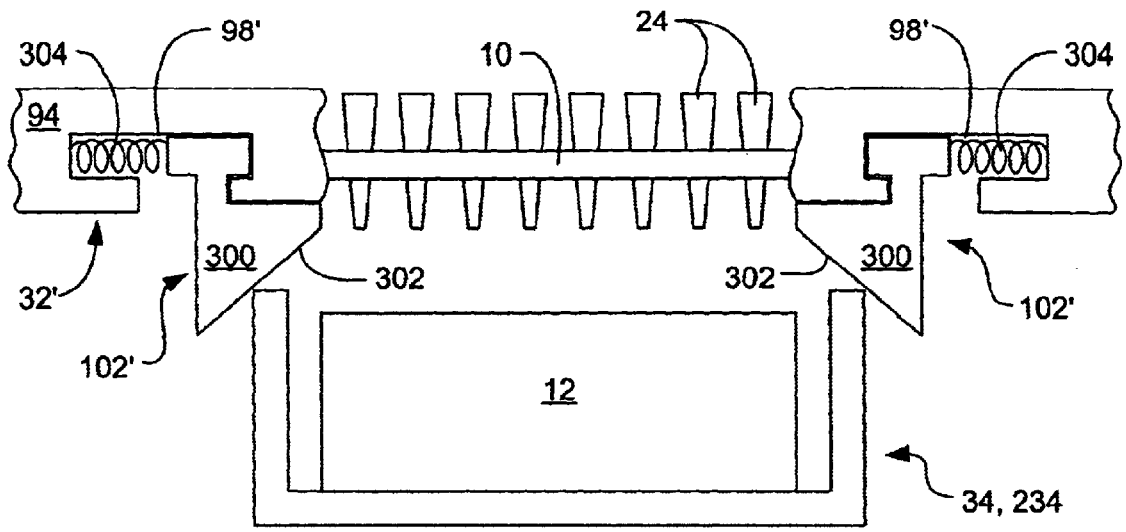
FIG. 13 is a front view of an alternative embodiment of the inventive device wherein the frame of the dispenser utilizes horizontally oriented slots containing springs and the ends of the capture blades incorporate trapezoidal exterior members.
Figure 14:
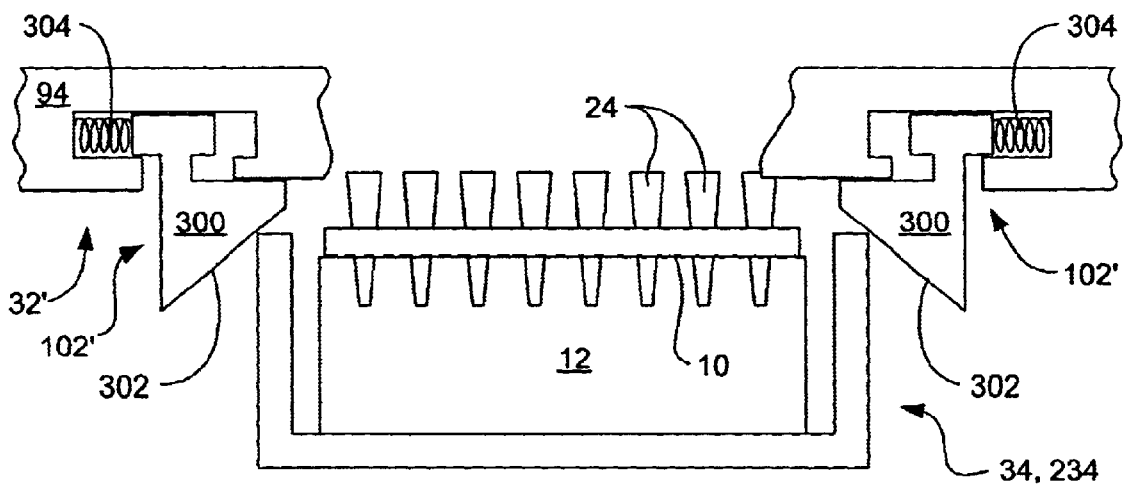
FIG. 14 is a front view of the alternative embodiment of FIG. 13 wherein the garage has been lifted to force the trapezoidal exterior members outwardly, thereby opening the capture blades of the dispenser.

It should be understood that any of the dispenser embodiments used in the inventive devices described herein could use alternative means to open and close the capture blades. For example, as shown in FIGS. 13 and 14, an alternative dispenser 32' constructed in the same fashion as dispenser 32 except as provided below, uses camming slots 98' which are horizontally oriented rather than upwardly sloped, and uses blade ends 102'. Blade ends 102' each form an outer member 300 outside frame 94 which is generally trapezoidal and forms a lower surface 302 which is angled outwardly in relation to camming slots 98'. As gravity does not operate to force the capture blades to their inward position to hold flats 10 within dispenser 32', dispenser. 32' comprises springs 304, which may be fitted within camming slots 98' as shown, which bias the blade ends 102' of capture blades 92' to the innermost position within camming slots 98', holding the capture blades in their closed position and retaining flat 10 within dispenser 32'. Alternatively, or in addition to springs 304, springs may be mounted at the outermost edges of aperture 124 to bias blade ends 102' inwardly (not shown). When garage 34, 234 is raised such that it first contacts members 150 of blade ends 102', members 300 cannot move upwardly because blade ends 102' cannot move upwardly within camming slots 98'. Because the lower surfaces 302 of members 300 are angled, once sufficient upward force is exerted upon garage 34, 234, members 300 will slide outwardly as shown in FIG. 14 against the resistance exerted by springs 304, opening the capture blades 92' and allowing flat 10 to fall onto rack 12.

It should also be noted that each embodiment of the inventive dispenser used herein can be constructed to accommodate platforms of a range of predetermined sizes and shapes, and to orient the platforms within the dispenser as desired. For example, while the devices 30 and 230 as shown orient the pipette tip flats 10 such that the longer side of the flats 10 align with the front of the device 30, 230 and the shorter side of the flats 10 align with the sides of the device 30, 230, each device 30, 230 can easily be constructed to hold the flats 10 in the opposite orientation.

Further, it should also be noted that for each of the above-described embodiments of the inventive device, it is not necessary to utilize a housing physically connecting the dispenser and the garage, or to employ guides with the dispenser. Rather, the dispenser may be separately mounted by the user wherever desired, and the garage may be brought underneath the dispenser to release a unit of platform-loaded goods onto a rack stored within the dispenser.

Figure 15:
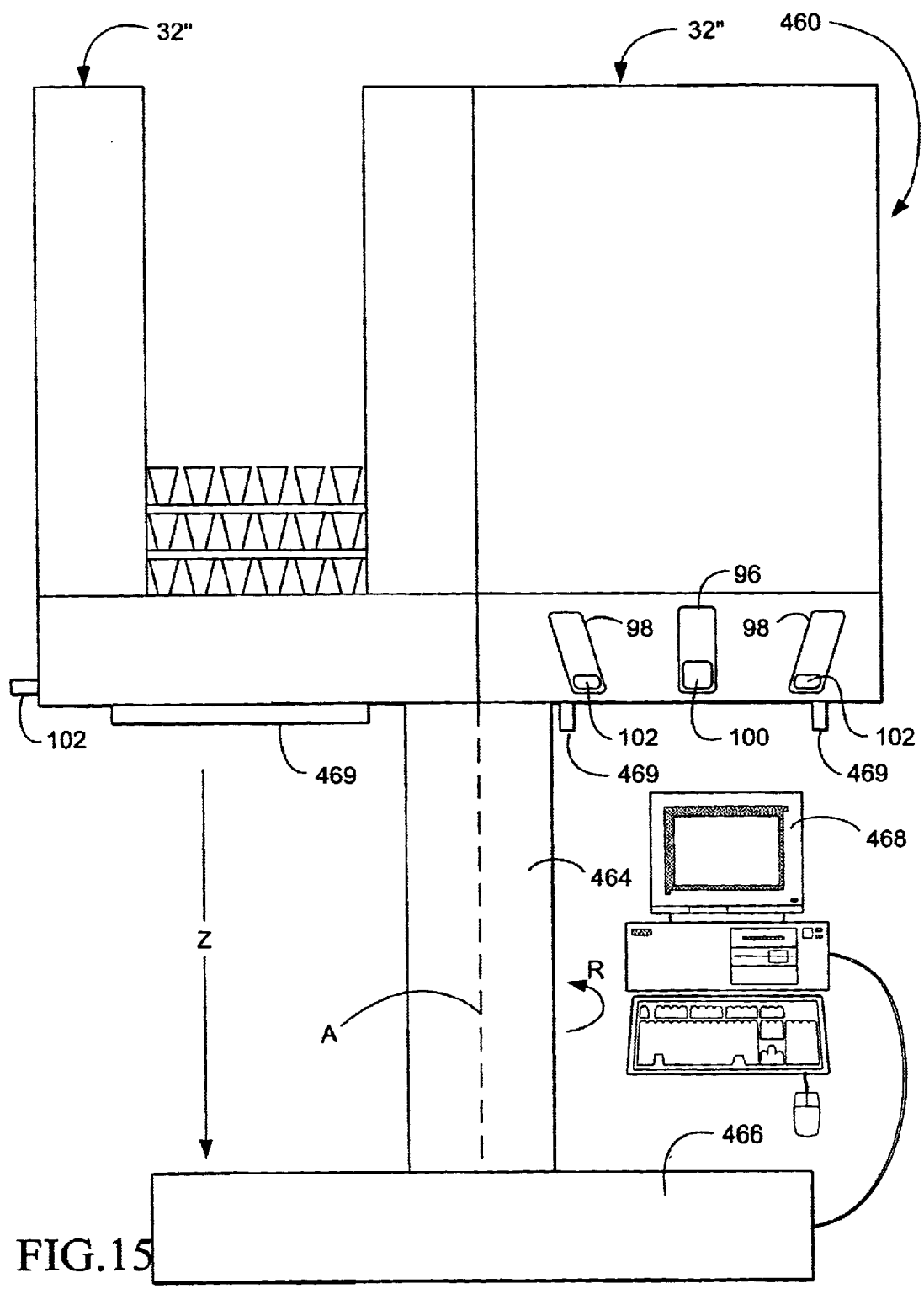
FIG. 15 is a side elevation view of an alternative embodiment of the inventive device wherein four dispensers are incorporated into a rotatable platform to dispense four stacks of platform-loaded goods.

Additionally, multiple dispensers may be arranged together for convenient access. This can be of particular utility where the inventive device is used with a robotic system. Referring to FIG. 15, a preferred automated four-dispenser rotary platform 460 is shown which may be incorporated into the automated pipette tip delivery system 462 shown in FIG. 16. Rotary platform 460 comprises four dispensers 32" mounted upon a central rod 464 which is in turn mounted upon a rotary table 466. Rotary table 466 is operable by a control system 468 to rotate in at least one direction R around the vertical axis A defined by rod 464, thereby rotating rod 464 and dispensers 32". Control system 468 may comprise any means suitable for activating and controlling the rotary table 466, including manual controls. However, preferably control system 468 constitutes a separate microprocessor or computer, which may be fixed to or incorporated into the rotary platform 460, but which is preferably located nearby the rotary platform 460 at an accessible station.

The preferred dispensers 32" used in rotary platform 460 are substantially identical to dispenser 32, except that each dispenser 32" has two skirts 469 downwardly extending from the lower surface of its inner portion 90. The skirts 469 of each dispenser 32" are designed for use in conjunction with a robotic gripper, described below, and are positioned such that when the capture blades of the dispenser 32" are open, the skirts 469 do not impede the passage of a pipette tip flat 10 through the aperture of the dispenser 32".

Figure 16:
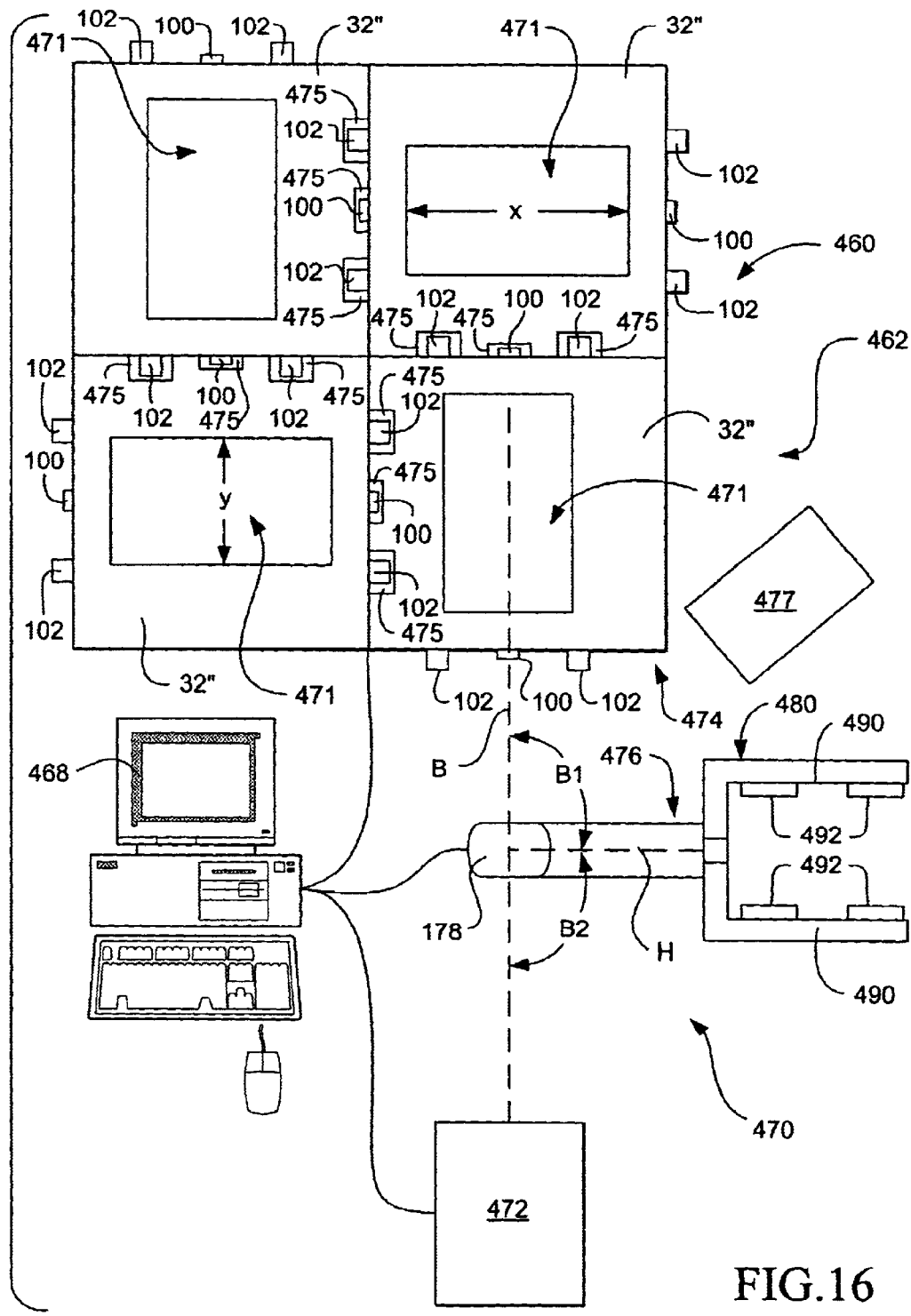
FIG. 16 is a top plan view of the platform of FIG. 15 used in conjunction with an automated pipette tip delivery system.

As shown in FIG. 16, automated system 462 preferably comprises rotary platform 460, a rotatable robotic pipette tip flat pick-up unit 470, and a delivery site to which pipette tips and/or pipette tip flats are delivered. The delivery site may comprise a robotic pipettor 472 designed to remove and process pipette tips from the pipette tip flats picked up by the pick-up unit 470. Such robotic pipettors include, but are not limited to: 96 barrel pipettors such as the Cyclone pipettor available from Scitec, Inc. of Wilmington, Delaware, the MultiMek pipettor available from Carl Creative of Harbor City, or the Cyberlab 96 Well Pipetting Workstation from Cyberlab, Inc. of Brookfield, Conn.; and flexible pipettors (which pick up four to eight pipette tips from a flat at a time) such as the Genesis pipettor available from Tecan or RTP, North Carolina; the Biomek 2000 pipettor available from Beckman of Fullerton, Calif., California; or the Multi-PROBE pipettor available from Packard Instrument Co. of Meriden, Conn. However, it should be understood that the delivery site may comprise any location to which pick-up device 470 may deliver pipette tips or pipette tip flats and may utilize any desired device for retrieving or otherwise processing those tips or flats from the pick-up device 470.

Dispensers 32" each form a rectangular central aperture 471 having a longer axis X and a shorter axis Y to accommodate the passage of a standard pipette tip flat. As shown in FIG. 13, each dispenser 32" is preferably oriented at a 90 degree rotation with respect to the adjoining two dispensers 32". Accordingly, with respect to any selected quadrant 474 of rotary platform 460, every time the rotary platform 460 is rotated by 90 degrees, the new dispenser 32" rotated into the quadrant 474 will have the same orientation as the dispenser 32" rotated out of the quadrant 474. Dispensers 32" may be arranged in this configuration with slight spacing between them so that the post 100 and blade ends 102 of one dispenser 32" do not strike the side of the adjoining dispenser 32", or, as shown in FIG. 13, channels 475 may be cut into the side of the adjoining dispenser 32" to accommodate posts 100 and blade ends 102.

Preferred pick-up unit 470 comprises a gripper unit 476, a rotator to rotate the gripper unit 476, and a vertical lifter 478 operable to lift all or part of the gripper unit 476 vertically along axis Z (shown in FIG. 15). It should be understood that while it is preferred that the rotator be capable of rotating the gripper unit 476 over at least a 180 degree range, defined by axis B and arcs B1 and B2, any rotator may be used which is capable of moving the gripper unit 476 between quadrant 474 and any desired delivery site. Vertical lifter 478 preferably is operable to lift the entire gripper unit 476 along the Z axis, but could alternatively, for example, be operable to raise and lower only the head portion 480 of the gripper unit 476.

Figure 17:
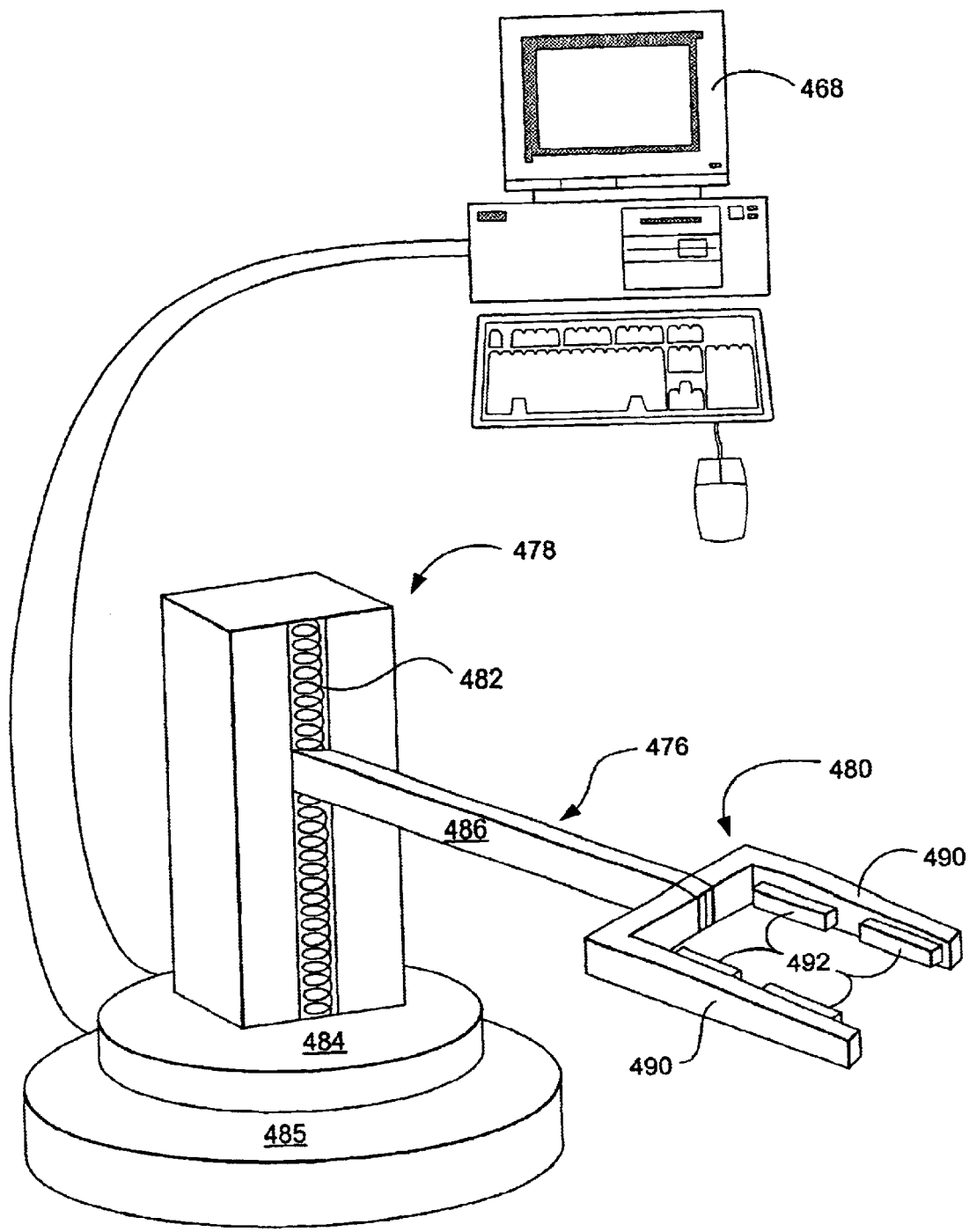
FIG. 17 is a perspective view of a robotic pick-up device used in the automated pipette tip delivery system of FIG. 16.

Referring to FIG. 17, the vertical lifter 478 of the pick-up unit 470 may comprise a vertically oriented actuator 482 to which the gripper unit 476 is connected such that the gripper unit 476 can be raised or lowered along the Z axis upon operation of the actuator 482. The rotator for rotating the gripper unit 476 may comprise a second rotary table 484 which rotates the entire pick-up unit 470. However, it should be understood that the vertical lifter can comprise any means for raising and lowering the gripper unit 476, including but not limited to pneumatically driven lifters, and the rotator can comprise any means for rotating the pick-up unit 470, including but not limited to a rotation means such as a stepping motor or servomotor (not shown) fitted between the arm 486 (see FIG. 16) and the connection of the gripper unit 476 to the actuator 482 (see FIG. 17). Like rotary table 466, the vertical lifter 478 and rotator are preferably controlled by central control system 468, but each could alternatively be operated using local controllers.

It should be understood that the pick-up unit 470 may be equipped with additional automated features if desired to allow the pick-up unit 470 or its various parts to move along additional axes. For example, pick-up unit 470 could incorporate a horizontal mover operable to move the gripper unit 476 horizontally rather than rotationally in order to allow the gripper to secure other objects. However, it is more costeffective to exclude such additional features where they are not necessary to the functioning of the automated system, as in the preferred automated system 462.

Gripper unit 476 preferably comprises two gripper arms 490 and means for closing and opening the gripper arms 490. The means for closing and opening the gripper arms 490 is preferably controlled by control system 468, and may operate pneumatically, electrically, or by any other means known in the art. Gripper arms should be positionable such that when the gripper unit 476 is positioned below a dispenser 32" in quadrant 474, gripper arms 490 will contact skirts 469 when the gripper unit 476 is raised, thereby dispensing a pipette tip flat as will be described below. Gripper arms 490 each preferably form inwardly extending lips 492 such that when gripper arms 490 come into contact with skirts 469 to release a pipette tip flat, the flat will fall onto and be supported by lips 492.

Referring to FIG. 16, pick-up unit 470 is positioned in relation to rotary platform 460 such that when rotary platform 460 is rotated to bring the longer X axis of one of the dispensers 32" into alignment with axis B, gripper unit 476 may be rotated into a position where gripper arms 490 of pick-up unit 470 will align with the dispenser 32" in quadrant 474. Accordingly, when the vertical lifter 478 is then operated to lift gripper unit 476, the gripper arms 490 engage skirts 469 (see FIG. 15) and lift the inner portion of the dispenser 32", forcing blade ends 102 to slide upwardly within the slots in the dispenser frame, thereby forcing the capture blades open. One or more of the flats loaded into the dispenser 32" will then fall onto the lips 492 of gripper unit 476. The number of flats loaded onto the gripper unit 476 in this matter will be dependent upon the distance the flats fall, which will be defined by the length of the skirts 469 on the dispenser and the distance between the upper surface of the gripper arms 490 and of the lips 492.

It should be understood that the dispenser can utilize any number of skirts or any size or shape of skirt, provided that the skirt or skirts does not impede dispensing flats from the dispenser, and that when the skirt or skirts is contacted by the gripper unit or other structure engaging the dispenser to release flats (such as a garage), the inner portion of the dispenser is lifted such that the capture blades of the dispenser are retracted evenly.

In operation, control system 468 is preferably programmed to control rotary tables 466 and 484, actuator 482, and the means for opening and closing gripper arms 490. Each dispenser 32" of rotary platform 460 is filled with a preselected number of pipette tip flats, and control system 468 operates rotary table 466 such that one of the dispensers 32" is positioned in quadrant 474. Control system 468 then operates actuator 482 to lower gripper unit 476 and rotate gripper unit 476 such that it is positioned in quadrant 474 below the dispenser 32". This is the "home" position for the automated system 462.

In the preferred embodiment, the pipette tip flat delivery process is started by a signal to the control system 468 from the robotic pipettor 472 that the pipettor is ready to process a new flat of pipette tips. However, it should be understood that the control system may be activated to start the delivery process by other means, including but not limited to receiving input from a human user through manual controls. The control system then activates the actuator 482 to raise the pick-up unit 476 by a preselected distance which brings the gripper arms 490 into contact with the skirts 469 of the dispenser 32" at quadrant 474, releasing a pipette tip flat onto lips 492.

The control system 468 then activates the actuator 482 to lower the pick-up unit 476 to the home position, and controls the pick-up unit's rotary table 484 to rotate the pick-up unit 476 through arcs B1 and B2 to the automated pipettor 472. The control system 468 leaves the pick-up unit 476 in that position until the automated pipettor 472 is finished processing the pipette tips in the flat atop the lips 492. Preferably the automated pipettor 472 signals the control system 468 when it is done processing the flat. However, alternative methods could also be used to determine the time the control system 468 retains the pick-up unit 476 in position at the pipettor 472, including but not limited to waiting for a preselected amount of time for the pipettor 472 to finish processing.

The automated pipettor 472 or other device to which the pipette tip flat is delivered may be designed to remove all of the pipette tips from the pipette tip flat and also to remove the pipette tip flat from the pick-up unit 476. In that case, upon completion of processing by the pipettor 472, the control system rotates the pick-up unit 476 back to the home position by activating rotary table 484. However, typically the automated pipettor 472 will remove the pipette tips from the flat but leave the flat atop lips 492. It should also be understood that the pipettor 472 or other device could be designed to inject material into the pipette tips and to leave the pipette tips within the flat on lips 492, or to replace pipette tips removed from the flat with other pipette tips. In that instance, once processing of the pipette tip flat by pipettor 472 is completed, control system 468 may be programmed to activate rotary table 484 to another station at which the pipette tip flat is removed from lips 492. For example, a flat recovery station (not shown) could be positioned at location 477 at which empty flats may be dropped from the pick-up unit 476 by activating the means for opening the gripper arms 490 to open the gripper arms until the flat falls through lips 492. However, it should be noted that additional means may be used to remove flats from lips 492, including but not limited to providing a stripper device at location 477 which will pick up the pipette tip flat from lips 492 when the actuator 482 is operated to lift the pick-up unit 476 to a high position on actuator 482, or providing the pick-up unit 476 with means for rotation about axis H, such that empty flats may be dumped off of lips 492 by inverting the pick-up unit 476. It should be understood that should alternative means for releasing flats from pick-up unit 476 be used, it may not be necessary to include the means for opening and closing gripper arms 492.

After the flat on the pick-up unit 476 has been removed, by pipettor 472, at location 477, or otherwise, the control system 468 then activates actuator 484 to lower the pick-up unit 476 and activates rotary table 484 to move pick-up unit 476 back into the home position.

It should be understood that other stations for processing the pipette tips and/or flat may be placed along the path of rotation of pick-up unit 476 and that the control system may be programmed to move the pick-up unit 476 into position at those stations to accommodate the further processing. The number of stations which may be placed upon the path of rotation may be increased, for example, by increasing the length of the rotator arm 486 to lengthen the path of rotation.

The foregoing describes the completion of one dispensing cycle of a single flat from the dispenser 32" at quadrant 474. As the control system is directed to process additional flats of pipette tips, the control system 468 first checks to determine whether there is a pipette tip flat in the dispenser 32" positioned at quadrant 474. One method for enabling the control system 468 to make that determination is to initialize the control system 468 before operation with the number of flats loaded into each dispenser 32". In that case, at some point such as the end of each dispensing cycle, control system 468 records that the number of flats in the dispenser 32" at quadrant 474 has been reduced by one. Accordingly, the control system 468 can check its program variables to determine whether the number of flats in the dispenser 32" at quadrant 474 has been reduced to zero. As another example, alternatively or in addition to using program variables, a sensor may be utilized which determines whether a flat is present in the dispenser 32" at quadrant 474.

If a pipette tip flat is present in the dispenser 32" at quadrant 474, control system 468 completes another dispensing cycle as described above. If no pipette tip flats are present in the dispenser 32" at quadrant 474, control system 468 operates rotary table 466 to rotate rotary platform 460 until a dispenser 32" in which at least one pipette tip flat is present is located at quadrant 474, and then completes another dispensing cycle. If no pipette tip flats are present in any dispenser 32", control system 468 is preferably programmed to cease operation and is preferably provided with an alarm which the control system then activates to alert the user that operation has ceased. One advantage of the above-described rotary platform 460 and automated system is that the dispensers 32" not being processed (those dispensers 32" not positioned at quadrant 474) may be refilled with pipette tip flats during operation of the system to dispense flats from the dispenser 32" at quadrant 474.

Figure 18:
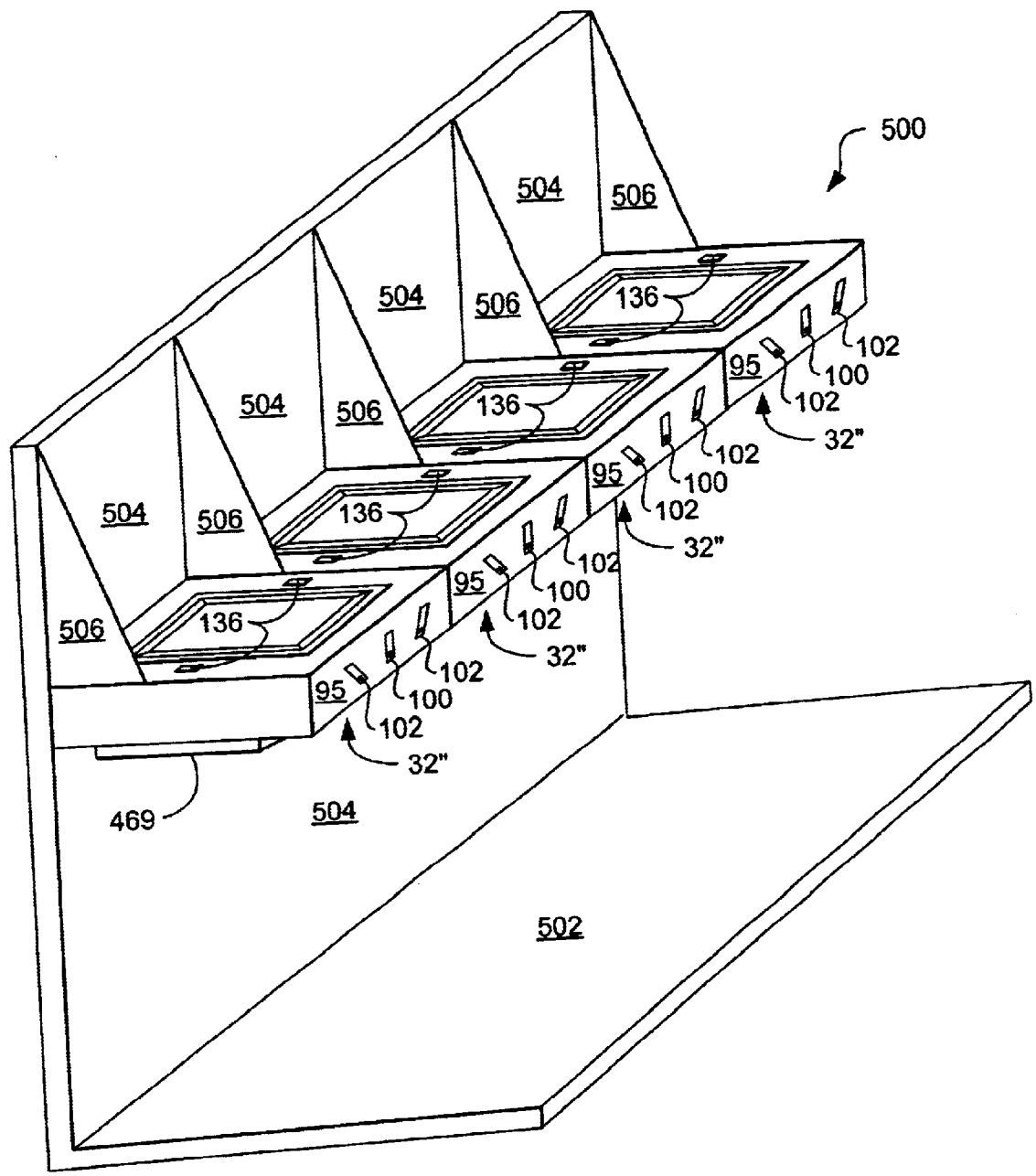
FIG. 18 is a perspective view of a linear multi-dispenser platform.

It should be understood that a variety of multiple-dispenser assemblies can be constructed for either automated or manual use. For example, a preferred four-dispenser linear platform 500 is shown in FIG. 18. Linear platform 500 comprises a base 502, rear wall 504, guides 506 and dispensers 32". Dispensers 32" may be fastened to rear wall 504 using fasteners, adhesives, or the like, or may be formed integrally therewith. The sides 95 of the dispensers 32" facing rear wall 504 should be attached to the wall 504 such that sufficient spacing is provided to allow for movement of blade ends 102 extending from those sides 95 when dispensers 32" are in operation. Guides 506 are attached to the upper surface of dispensers 32", and act both to support dispensers 32" on rear wall 504 and to assist in guiding pipette tip flats into the respective dispensers 32". As in rotary platform 460, dispensers 32" preferably comprise skirts 469 allowing the dispensers to be activated by gripper units such as gripper unit 476.

In operation, one or more of dispensers 32" of linear platform 500 are loaded with pipette tip flats. In automated use, linear platform 500 may be used with one or more robotic pick-up devices, each of which should be operable to position itself below at least one of dispensers 32" and to trigger dispensing of one or more pipette tip flats by engaging the skirts 469 of the dispenser 32". It should be understood that a variety of robotic assemblies could be used in conjunction with linear platform 500. For example, one robotic pick-up device could correspond to each dispenser 32, or a single pick-up device could be used with all four dispensers 32". It should also be understood that linear platform 500 can be adapted to include any number of dispensers 32"; the use of four dispensers 32" herein is merely chosen as a particular example.

Figure 19:
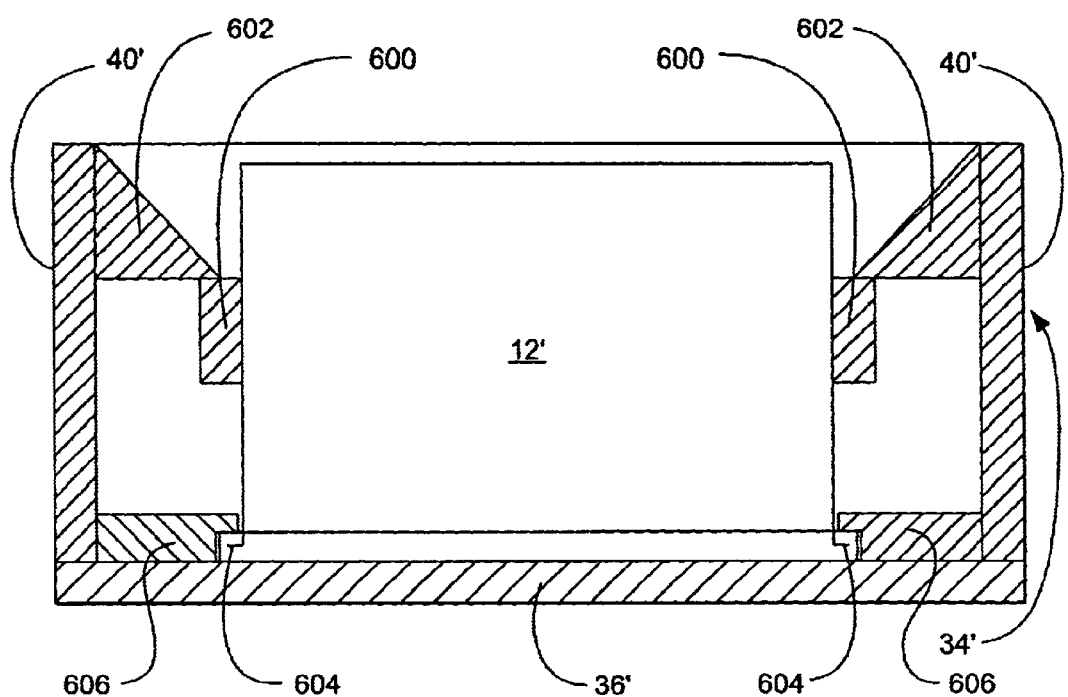
FIG. 19 is a front cross-sectional view of an alternative embodiment of the garage of the inventive device which may be used in conjunction with a robotic pick-up device.

With each of the described automated systems, it should be understood that the system could use dispensers that do not include skirts 469, and which instead utilize pick-up devices which hold a garage which is used to activate the dispenser. For example, FIG. 19 depicts a preferred embodiment of a garage 34' designed for use with a gripper unit comprising gripper arms 600. Garage 34' has base 36', side walls 40', and a rear wall, and forms two downwardly and inwardly extending flanges 602 from the upper edge of its side walls 40'. Flanges 602 extend inwardly such that a rack 12 of the desired size can fit between them without substantial clearance. In operation, gripper arms 600 are inserted into garage 34' such that they are positioned underneath flanges 602. If a rack 12 is already present in garage 34', gripper arms 600 should be positioned to be adjacent to two opposing sides of rack 12 as shown in FIG. 15. Accordingly, once gripper arms 600 are lifted (for example, by using a vertical lifter such as lifter 478), gripper arms 600 will engage the undersides of flanges 602, thereby lifting garage 34'. If the gripper arms 600 are capable of opening and closing, they are preferably tightened to capture rack 12 between them. If it is desired that the position of rack 12 within garage 34' be further secured and a rack 12 is used which forms lower lips 604 on either side, members 606 may be formed within garage 34' to engage lips 604 underneath members 606. When the gripper unit is used to release a flat from the dispenser, the pick-up unit is positioned beneath the dispenser such that the walls 40' of garage 34' align with the blade ends of the dispenser's capture blades, and gripper arms 600 are lifted, bringing walls 40' into contact with the blade ends of the dispenser and releasing a flat in the manner previously described in relation to FIGS. 9 and 10.

Figure 20:
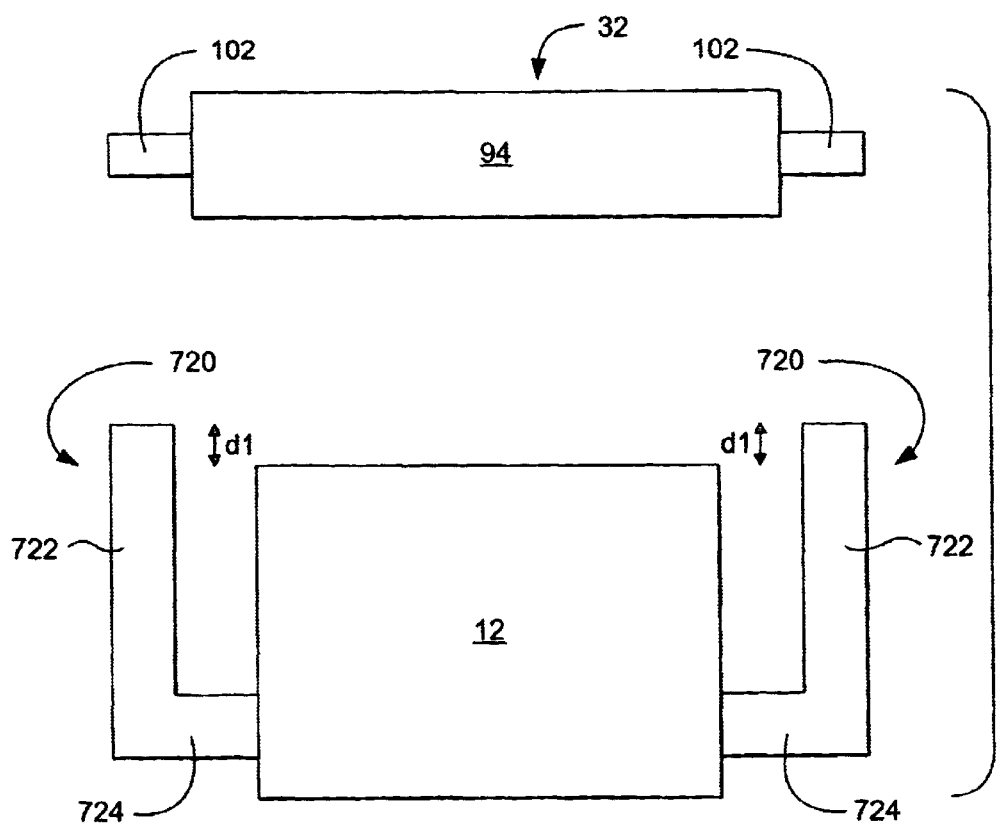
FIG. 20 is a side elevation view of an embodiment of the inventive dispenser used in conjunction with a robotic gripper having gripper arms with vertically extending prongs, the gripper arms securing a pipette tip rack.
Figure 21:
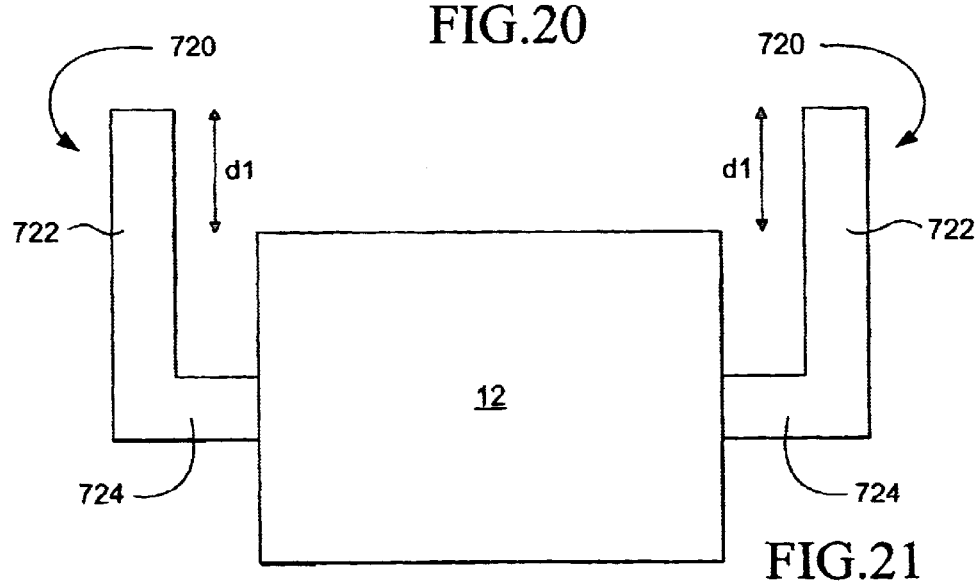
FIG. 21 is a side elevation view of the gripper arms of FIG. 20 securing the pipette tip rack in a different position.

FIGS. 20–21 illustrate another alternative embodiment suitable for automated dispensing of pipette tip flats from a dispenser 32, wherein the gripper arms of a gripper holding a pipette tip rack incorporate structures which engage blade ends 102 of the dispenser 32. Referring to FIG. 20, rack 12 is gripped by a robotic gripper having gripper arms 720 each comprising an upraised prong 722 and a head 724 which engages the side of the rack 12. When gripper arms 720 are closed to engage rack 12, the heads 724 of the gripper arms should be positioned with respect to rack 12 such that the tops of prongs 722 extend a desired distance d1 above the upper surface of rack 12. When the robotic gripper is operated to lift gripper arms 720, and thereby to lift rack 12, until prongs 722 engage blade ends 102 of the dispenser, the capture blades of the dispenser will open, allowing one or more pipette tip flats, as determined by the distance d1, to fall onto rack 12. When the gripper arms 720 are again lowered, the capture blades of the dispenser will close to capture the remaining flats in the stack of pipette tip flats held within the dispenser. The distance d1 between the top of the prongs 722 and the upper surface of the rack 12 may readily be changed by altering the placement of heads 724 of gripper arms 720 with respect to the rack 12. For example, as shown in FIG. 21, d1 may be increased by engaging heads 724 at a higher point along the sides of rack 12.

The various embodiments of the dispensers, garage and housing can be simply and affordably constructed using one or more metals. However, it should be understood that those embodiments could also be constructed from any durable material, such as plastics, wood, or the like.

Although the foregoing invention has been described in some detail by way of illustration for purposes of clarity of understanding, it will be readily apparent to those of ordinary skill in the art in light of the teachings of this invention that certain changes and modifications may be made thereto without departing from the spirit or scope of the appended claims.

It is claimed:

1. A device for dispensing units of platform-loaded goods from a stack of one or more units of platform-loaded goods, comprising:

a dispenser, said dispenser including a dispenser frame forming a central aperture, said central aperture defining a plane and having sufficiently large dimensions to allow passage of one of said units of platform-loaded goods therethrough when said unit of platform-loaded goods is maintained in parallel with said plane, capture blades for retaining said stack within said dispenser when said capture blades are in a closed position and for releasing said stack such that units of platform-loaded goods in said stack can pass through said aperture when said capture blades are in an open position, and blade control means for opening and closing said capture blades, said blade control means biased to hold said capture blades in said closed position;

means for engaging said dispenser such that said blade control means are moved upwardly in relation to said dispenser frame to open said capture blades, allowing one or more units of platform-loaded goods in said stack to fall through said aperture.

2. The device of claim 1 wherein said means for engaging said dispenser comprises holding means for holding a receptacle for one or more of said units of platform-loaded goods, said holding means capable of engaging said blade control means such that when a receptacle is held by said holding means and said holding means engages said blade control means, said blade control means opens said capture blades sufficiently to allow one or more units of platform-loaded goods in said stack to fall through said aperture and onto said receptacle.

3. The device of claim 2 wherein said holding means is a garage.

4. The device of claim 3 further comprising a housing, said garage movably secured to said housing such that said garage can be raised and lowered over a range, said housing positioned in relation to said dispenser such that said garage can be raised to a point within said range wherein said garage will engage said blade control means of said dispenser and cause said blade control means to open said capture blades and lowered to a point within said range wherein said garage does not engage said blade control means.

5. The device of claim 4 wherein said housing comprises at least one vertically oriented alignment slot and said garage comprises at least one alignment member slidably engaged within said at least one alignment slot such that said garage is maintained in a fixed orientation with respect to said housing when said at least one alignment member slides within said at least one alignment slot and said garage can be raised and lowered over said range.

6. The device of claim 5 wherein said alignment member comprises a tongue.

7. The device of claim 5 wherein said alignment member comprises a grip.

8. The device of claim 5 wherein said dispenser frame forms four sides, wherein said blade control means comprises a pair of camming slots formed in each of two opposing sides of said dispenser frame, said camming slots angled upwardly and outwardly, said pair of camming slots of one said opposing side aligning with said pair of camming slots of said other opposing side, and wherein said blade control means further comprises opposing blade ends of each of said capture blades, said blade ends of each capture blade engaged within two opposing aligned camming slots.

9. The device of claim 8 further comprising a lifting member operable to raise and lower said garage within said housing.

10. The device of claim 9 wherein said garage has a plurality of sides including at least a pair of opposing sides, said opposing sides each having an upper edge and further comprising a flange positioned adjacent or proximate to said upper edge, each said flange having a lower surface, said flanges extending inwardly such that when a receiver for receiving one or more of said units of platform-loaded goods is held in two opposing gripper arms of a robotic device and said robotic device is activated to place said receiver within said garage between said flanges and said gripper arms are raised to lift the receiver, said gripper arms will engage the lower surfaces of said flanges and raise said garage.

11. The device of claim 10 wherein said platform-loaded goods are pipette tip flats loaded with pipette tips and wherein said receiver is a pipette tip rack.

12. The dispenser platform of claim 9 further comprising means for engaging a dispenser positioned in said region such that the blade control means of said dispenser are moved upwardly in relation to said dispenser frame to open said capture blades, allowing one or more units of platform-loaded goods in the stack in said dispenser to pass through the aperture of said dispenser.

13. The dispenser platform of claim 12 wherein said means for engaging a dispenser positioned in said region comprises a robotic gripper comprising at least two opposing gripper arms.

14. The dispenser platform of claim 13 wherein said means for engaging a dispenser positioned in said region comprises holding means for holding a receptacle for one or more of said units of platform-loaded goods, said holding means capable of engaging said blade control means such that when a receptacle is held by said holding means and said holding means engages said blade control means, said blade control means opens said capture blades sufficiently to allow one or more units of platform-loaded goods in the stack in said dispenser to pass through the aperture of said dispenser and onto said receptacle.

15. The dispenser platform of claim 12 wherein said platform-loaded goods are pipette tip flats each loaded with an array of pipette tips.

16. A device for dispensing units of platform-loaded goods from a stack of one or more units of platform-loaded goods, comprising:

a dispenser, said dispenser including a dispenser frame forming a central aperture, said central aperture defining a plane and having sufficiently large dimensions to allow passage of one of said units of platform-loaded goods therethrough when said unit of platform-loaded goods is maintained in parallel with said plane, capture blades for retaining said stack within said dispenser when said capture blades are in a closed position and for releasing said stack such that units of platform-loaded goods in said stack can pass through said aperture when said capture blades are in an open position, and blade control means for opening and closing said capture blades, said blade control means biased to hold said capture blades in said closed position;

a robotic gripper comprising at least two opposing gripper arms for engaging said dispenser such that said blade control means are moved upwardly in relation to said dispenser frame to open said capture blades, allowing one or more units of platform-loaded goods in said stack to fall through said aperture.

17. The device of claim 16 wherein said robotic gripper is operable to close said gripper arms to secure a receptacle between them and to open said gripper arms to release said receptacle.

18. The device of claim 16 wherein said dispenser further comprises at least one skirt downwardly extending from said dispenser frame.

19. The device of claim 18 wherein said stack of units of platform-loaded goods forms a lowermost unit, and wherein each of said at least two opposing gripper arms forms an inwardly extending lip, such that when said robotic gripper engages said dispenser to allow one or more units of platform-loaded goods in said stack to fall through said aperture, said lowermost unit is received upon said inwardly extending lips.

20. An automated dispensing system for dispensing units of platform loaded goods, comprising:

at least one dispenser, each dispenser including a dispenser frame forming a central aperture, said central aperture defining a plane and having sufficiently large dimensions to allow passage of one of said units of platform-loaded goods therethrough when said unit of platform-loaded goods is maintained in parallel with said plane, capture blades for retaining a stack of said units of platform-loaded goods within said dispenser when said capture blades are in a closed position and for releasing said stack such that one or more units of platform-loaded goods in said stack can pass through said aperture when said capture blades are in an open position, and blade control means for opening and closing said capture blades, said blade control means biased to hold said capture blades in said closed position;

engaging means for engaging each dispenser such that its blade control means are moved upwardly in relation to its dispenser frame to open its capture blades, allowing its stack to fall through its aperture;

means for moving said engaging means over a first range, such that within said first range said engaging means can be positioned with respect to at least one dispenser such that if it is raised it will engage the dispenser, and such that said engaging means also can be positioned at a delivery site;

lifting means for moving said engaging means vertically over a second range, such that within said second range said engaging means can be moved into and out of engagement with said at least one dispenser;

a control system for operating said means for moving said engaging means and said lifting means.

21. The automated dispensing system of claim 20 wherein said means for moving said engaging means comprises a rotation means.

22. An automated dispensing system for dispensing units of platform loaded goods, comprising:

at least one dispenser, each dispenser including a dispenser frame forming a central aperture, said central aperture defining a plane and having sufficiently large dimensions to allow passage of one of said units of platform-loaded goods therethrough when said unit of platform-loaded goods is maintained in parallel with said plane, capture blades for retaining a stack of said units of platform-loaded goods within said dispenser when said capture blades are in a closed position and for releasing said stack such that one or more units of platform-loaded goods in said stack can pass through said aperture when said capture blades are in an open position, and blade control means for opening and closing said capture blades, said blade control means biased to hold said capture blades in said closed position;

engaging means for engaging each dispenser such that its blade control means are moved upwardly in relation to its dispenser frame to open its capture blades, allowing its stack to fall through its aperture;

means, comprising a rotation means, for moving said engaging means over a first range, such that within said first range said engaging means can be positioned with respect to at least one dispenser such that if it is raised it will engage the dispenser, and such that said engaging means also can be positioned at a delivery site;

lifting means for moving said engaging means vertically over a second range, such that within said second range said engaging means can be moved into and out of engagement with said at least one dispenser; and a control system for operating said means for moving said engaging means and said lifting means;

wherein said automated dispensing system comprises at least a plurality of said dispensers, said dispensers together forming a dispenser assembly such that at least one region of the dispenser assembly is defined wherein when the dispenser assembly is rotated each dispenser in said assembly may successively be positioned within said region and activated to release a unit of platform-loaded goods when said engaging means is positioned within said region and lifted to engage the dispenser, and wherein said automated dispensing system further comprises means for rotating said dispenser assembly, said control system operating said means for rotating said dispenser assembly.

23. The automated dispensing system of claim 22 wherein said engaging means is a garage.

24. The automated dispensing system of claim 23 wherein said engaging means is a robotic gripper comprising at least two opposing gripper arms.

25. The automated dispensing system of claim 24 wherein each dispenser further comprises at least one skirt downwardly extending from its dispenser frame.

26. The automated dispensing system of claim 25 wherein each of said opposing gripper arms of said robotic gripper forms an inwardly extending lip, such that when said robotic gripper engages one of said dispensers to allow one or more units of platform-loaded goods in its stack to fall through its aperture, the lowermost unit of platform-loaded goods in said stack is received upon said inwardly extending lips.

27. The automated dispensing system of claim 26 wherein said robotic gripper is operable to close said gripper arms to secure a receptacle between them and to open said gripper arms to release said receptacle.

28. A device for dispensing units of platform-loaded goods from a stack of one or more units of platform-loaded goods, comprising:

a dispenser, said dispenser including a dispenser frame forming a central aperture, said central aperture defining a plane and having sufficiently large dimensions to allow passage of one of said units of platform-loaded goods therethrough when said unit of platform-loaded goods is maintained in parallel with said plane, capture blades for retaining said stack within said dispenser when said capture blades are in a closed position and for releasing said stack such that units of platform-loaded goods in said stack can pass through said aperture when said capture blades are in an open position, and blade control means for opening and closing said capture blades, said blade control means biased to hold said capture blades in said closed position;

holding means for holding a receptacle for one or more of said units of platform-loaded goods, said holding means capable of engaging said blade control means such that when a receptacle is held by said holding means and said holding means engages said blade control means, said blade control means opens said capture blades sufficiently to allow one or more units of platform-loaded goods in said stack to pass through said aperture and onto said receptacle.

29. The device of claim 28 wherein said dispenser frame forms four sides, wherein said blade control means comprises a pair of camming slots formed in each of two opposing sides of said dispenser frame, said camming slots oriented horizontally, each of said camming slots defining an innermost and an outermost edge, said pair of camming slots of one said opposing side aligning with said pair of camming slots of said other opposing side, wherein said blade control further comprises springs fitted to each outermost edge of each camming slot, and wherein said blade control means further comprises opposing blade ends of each of said capture blades, said blade ends of each capture blade engaged within two opposing aligned camming slots and engaging such springs such that the spring of each camming slot exerts a force on said blade ends towards the innermost edge of the camming slot, said blade ends each forming an outer member extending outside the dispenser frame which forms a lower surface which is angled outwardly with respect to the camming slots.

30. An automated dispensing system for dispensing units of platform loaded goods, comprising:

at least one dispenser, said at least one dispenser defining a reference plane and including a central aperture sized to allow the units of platform loaded goods to pass therethough in a direction substantially perpendicular to said reference plane, said at least one dispenser including a pair of opposed walls each having at least one slot formed therein at an oblique angle to said reference plane;

an inner portion fitting within said at least one dispenser and capable of moving with respect to said at least one dispenser; and at least one capture blade supported within said inner portion and capable of moving with respect to said inner portion, said at least one capture blade including first and second ends fitting within said slots in said opposed walls, wherein movement of said inner portion with respect to said at least one dispenser moves said at least one capture blade with respect to said inner portion in a direction parallel to said reference plane.

31. An automated dispensing system as recited in claim 30, said at least one slot in each of said opposed walls comprising a first and second pair of slots, and said at least one capture blade comprising first and second capture blades, wherein movement of said inner portion with respect to said at least one dispenser moves said first and second capture blades closer or farther from each other in a direction parallel to said reference plane.

32. An automated dispensing system as recited in claim 30, further comprising a lifting member for engaging said inner portion and moving said inner portion with respect to said at least one dispenser in a direction perpendicular to said reference plane.

33. An automated dispensing system for dispensing units of platform loaded goods, comprising:

a dispenser, said dispenser defining a reference plane and including a pair of opposed walls and a central aperture sized to allow the units of platform loaded goods to pass therethough in a direction substantially perpendicular to said reference plane, said pair of opposed walls each including a first slot and a second slot formed therein at an oblique angle to said reference plane so that, in each wall, a first end of said first and second slots are spaced apart a greater distance than a second end of said first and second slots;

an inner portion fitting within said at least one dispenser and capable of moving with respect to said at least one dispenser in a direction perpendicular to said reference plane; and first and second capture blades supported within said inner portion and capable of moving with respect to said inner portion in a direction parallel to said reference plane, said first capture blade including first and second blade ends fitting within said first slots in said opposed walls, and said second capture blade including first and second blade ends fitting within said second slots in said opposed side walls, wherein movement of said inner portion in a first direction with respect to said at least one dispenser moves said first and second capture blades from a first position to a second position where said capture blades are farther apart from each other than in said first position.

34. An automated dispensing system as recited in claim 33, said aperture include a pair of spaced apart edges generally parallel to edges of said capture blades, wherein a distance between said capture blade edges is less than a distance between said aperture edges when said capture blades are in said first position.

35. An automated dispensing system as recited in claim 33, said aperture include a pair of spaced apart edges generally parallel to edges of said capture blades, wherein a distance between said capture blade edges is greater than a distance between said aperture edges when said capture blades are in said second position.

* * * * *